US012644882B2

(12) United States Patent
Feyeux et al.

(10) Patent No.: US 12,644,882 B2
(45) Date of Patent: Jun. 2, 2026

(54) CELLULAR MICROCOMPARTMENTS COMPRISING HUMAN CELLS UNDERGOING CARDIAC DIFFERENTIATION, TISSUES OBTAINED FROM SAID MICROCOMPARTMENTS AND USES THEREOF

(71) Applicant: TREEFROG THERAPEUTICS, Pessac (FR)

(72) Inventors: Maxime Feyeux, Talence (FR); Andrea Leonard, Pessac (FR)

(73) Assignee: TREEFROG THERAPEUTICS, Pessac (FR)

( * ) Notice: Subject to any disclaimer, the term of this patent is extended or adjusted under 35 U.S.C. 154(b) by 471 days.

(21) Appl. No.: 18/027,203

(22) PCT Filed: Sep. 21, 2021

(86) PCT No.: PCT/EP2021/075945
§ 371 (c)(1),
(2) Date: Jun. 28, 2023

(87) PCT Pub. No.: WO2022/058615
PCT Pub. Date: Mar. 24, 2022

(65) Prior Publication Data
US 2023/0358728 A1 Nov. 9, 2023

(30) Foreign Application Priority Data

Sep. 21, 2020 (FR) ..................................... 2009552

(51) Int. Cl.
*G01N 33/50* (2006.01)
*C12N 5/077* (2010.01)
(52) U.S. Cl.
CPC ....... *G01N 33/5061* (2013.01); *C12N 5/0657* (2013.01); *C12N 2501/415* (2013.01); *C12N 2506/45* (2013.01); *C12N 2513/00* (2013.01); *C12N 2533/74* (2013.01)
(58) Field of Classification Search
None
See application file for complete search history.

(56) References Cited

U.S. PATENT DOCUMENTS

2019/0330589 A1* 10/2019 Feyeux ................ C12N 5/0075

FOREIGN PATENT DOCUMENTS

WO WO2018096277 A1 5/2018

OTHER PUBLICATIONS

Jing, D., et al., "Cardiac Cell Generation From Encapsulated Embryonic Stem Cells in Static and Scalable Culture Systems", Cell Transplantation, Jun. 2, 2010, pp. 1397-1412, vol. 19.
Koivisto,J. et al., "Mechanically Biomimetic Gelatin-Gellan Gum Hydrogels for 3D Culture of Beating Human Cardiomyocytes", Applied Materials and Interfaces, May 23, 2019, pp. 20589-20602, vol. 11, No. 23.
Zhao, S., et al., "Bioengineering of injectable encapsulated aggregates of pluripotent stem cells for therapy of myocardial infarction", Nature Communications, Oct. 27, 2016, pp. 1-12, vol. 10, No. 1038.
Chang S., et al., "Emulsion-based encapsulation of pluripotent stem cells in hydrogel microspheres for cardiac differentiation", Biotechnology Progress, Feb. 28, 2020, vol. 36, No. 4. (fee).
Agarwal, P., et al., "A Biomimetic Core-Shell Platform for Miniaturized 3D Cell and Tissue Engineering", Aug. 2015, pp. 809-816, vol. 32, No. 8.
Abecasis, B., et al., "Toward a Microencapsulated 3D hiPSC-Derived in vitro Cardiac Microtissue for Recapitulation of Human Heart Microenvironment Features", Frontiers in Bioengineering and Biotechnology, Nov. 5, 2020, pp. 1-16, vol. 8.

* cited by examiner

*Primary Examiner* — Blaine Lankford
(74) *Attorney, Agent, or Firm* — Greer, Burns & Crain, Ltd.

(57) ABSTRACT

The invention relates to cellular microcompartments, each microcompartment successively comprising the following layers, which are organised around at least one lumen: —at least one inner layer of human cells undergoing cardiac differentiation, expressing at least one gene chosen from PDGFRα, MESP-1, NKX2-5, GATA4, MEF2C, TBX20, ISL1 and TBX5, —at least one intermediate layer of isotonic aqueous solution, and—at least one outer hydrogel layer. The invention also relates to the cardiac tissues obtained from said microcompartments and the use thereof, particularly in the treatment of heart disease.

16 Claims, 10 Drawing Sheets

12

14

20

250 µm

With no matrix added at time of encapsulation

With matrix added at time of encapsulation

CELLULAR MICROCOMPARTMENTS COMPRISING HUMAN CELLS UNDERGOING CARDIAC DIFFERENTIATION, TISSUES OBTAINED FROM SAID MICROCOMPARTMENTS AND USES THEREOF

CROSS-REFERENCE TO RELATED APPLICATIONS

This application is a U.S. National Stage Application of PCT/EP2021/075945 filed Sep. 21, 2021, claiming the benefit of priority from French patent application FR2009552 filed Sep. 21, 2020, the entire disclosure of both applications is herein incorporated by reference.

TECHNICAL FIELD

The invention relates to the treatment of cardiac diseases, in particular ischemic heart diseases, by the use of specific cardiac tissues obtained from particular cellular microcompartments comprising human cells expressing genes expressed during cardiac differentiation.

PRIOR ART

According to the World Health Organization, cardiovascular diseases, and in particular ischemic heart diseases (which generally lead to myocardial infarction), are the leading cause of death in the world (Thomas, H. et al. Global Atlas of Cardiovascular Disease 2000-2016: The Path to Prevention and Control. *Glob. Heart* 13, 143-163 (2018)).

Currently, there is no satisfactory solution for preventing or treating the consequences of cardiac ischemia and in particular for treating heart muscle necroses responsible for heart failure and risk of cardiac arrest.

Recently, research has been carried out on the use of cardiomyocytes derived from human pluripotent stem cells, hPSCs-CMs, which comprise both human embryonic stem cells and induced pluripotent stem cells, to regenerate lost or damaged cardiac tissues in order to avoid or treat associated heart failure (Desgres, M. & Menasché, P. Clinical Translation of Pluripotent Stem Cell Therapies: Challenges and Considerations. *Cell Stem Cell* 25, 594-606 (2019); Bertero, A. & Murry, C. E. Hallmarks of cardiac regeneration. *Nat. Rev. Cardiol.* 15, 579-580 (2018); Jiang, B., Yan, L., Shamul, J. G., Hakun, M. & He, X. Stem Cell Therapy of Myocardial Infarction: A Promising Opportunity in Bioengineering. *Adv. Ther.* 3, 1900182 (2020); Liew, L. C., Ho, B. X. & Soh, B. S. Mending a broken heart: Current strategies and limitations of cell-based therapy. *Stem Cell Res. Ther.* 11, 1-15 (2020)).

These cardiomyocytes may be used for other applications, in particular as biological cardiac stimulators for the treatment of sinus node dysfunction (Lee, J. H., Protze, S. I., Laksman, Z., Backx, P. H. & Keller, G. M. Human Pluripotent Stem Cell-Derived Atrial and Ventricular Cardiomyocytes Develop from Distinct Mesoderm Populations. *Cell Stem Cell* 21, 179-194.e4 (2017)), or for treating congenital heart diseases, such as septal abnormalities (Devalla, H. D. & Passier, R. Cardiac differentiation of pluripotent stem cells and implications for modeling the heart in health and disease. *Sci. Transl. Med.* 10, 1-14 (2018) or for the modeling of diseases, or for testing drugs and candidate drugs (Tzatzalos, E., Abilez, O. J., Shukla, P. & Wu, J. C. Engineered heart tissues and induced pluripotent stem cells:

Macro- and microstructures for disease modeling, drug screening, and translational studies. *Adv. Drug Deliv. Rev.* 96, 234-244 (2016)).

It is estimated that the amount of cells needed to regenerate the damaged cardiac tissues of a patient after myocardial infarction is about 1 billion (Laflamme, M. A. & Murry, C. E. Heart regeneration. *Nature* 473, 326-335 (2011), thereby making the use of hPSC-CM cardiomyocytes in cardiac cell therapy currently impossible on a suitable clinical scale. Indeed, producing cardiac tissues on an industrial scale is complex because it is necessary to achieve a compromise between culture conditions that are sufficiently mild for the survival and proper functioning of the tissues and large-volume culture constraints that inevitably expose the cells to non-physiological stresses (typically hydrodynamic stress in the context of liquid culture in bioreactors). The methods for producing cardiomyocytes from hPSC in particular have the following problems:

Poor formation of hPSC aggregates in suspension cultures prior to differentiation into cardiomyocytes; in fact the initial formation of hPSC aggregates and homogeneity are crucial for cellular reproduction and therefore for the quality of the cardiac tissue obtained after differentiation;

A significant loss of cells due to the sensitivity of the hPSCs to the shear stress and to the impacts during the culture in a bioreactor (Lam, A. T. L. et al. Conjoint propagation and differentiation of human embryonic stem cells to cardiomyocytes in a defined microcarrier spinner culture. *Stem Cell Res. Ther.* 5, 1-15 (2014));

The impossibility of combining a large-scale amplification of the hPSCs and cardiac differentiation (Le, M. N. T. & Hasegawa, K. Expansion culture of human pluripotent stem cells and production of cardiomyocytes. *Bioengineering* 6, (2019).

Known solutions for limiting these drawbacks during cardiac differentiation in suspension in a bioreactor requires:

either the use of microcarriers, as well as the temporary stopping of the agitation (Ting, S., Chen, A., Reuveny, S. & Oh, S. An intermittent rocking platform for integrated expansion and differentiation of human pluripotent stem cells to cardiomyocytes in suspended microcarrier cultures. *Stem Cell Res.* 13, 202-213 (2014))

or the use of cell lines less sensitive to shearing during cardiac differentiation (Laco, F. et al. Selection of human induced pluripotent stem cells lines optimization of cardiomyocytes differentiation in an integrated suspension microcarrier bioreactor. *Stem Cell Res. Ther.* 11, 1-16 (2020)).

However, these solutions are not optimal. In particular:

the microcarriers still leave the cells exposed to mechanical stresses and may be difficult to remove, the agitation does not allow for uniform diffusion of the nutrients and products necessary for differentiation, and limiting to a single starting cell line is extremely constraining and limiting.

It is also known that the loss of cells undergoing differentiation into cardiomyocytes can also be reduced by carrying out a culture directly in the bulk hydrogel (Kerscher, p. et al. Direct Production of Human Cardiac Tissues by Pluripotent Stem Cell Encapsulation in Gelatin Methacryloyl. *ACS Biomater. Sci. Eng.* 3.1499-1509 (2017); Li, Q. et al. Scalable and physiologically relevant microenvironments for human pluripotent stem cell expansion and differentiation. *Biofabrication* 10, (2018)), but these methods are not compatible with culture in a conventional bioreactor. In order to make the method compatible with bioreactors used in the industry, tests were carried out by encapsulating the cells in the hydrogel, but these tests were limited to mouse stem cells (Agarwal, P. et al. A Biomimetic Core-Shell Platform for Miniaturized 3D Cell and Tissue Engineering. *Part. Part. Syst. Charact.* 32, 809-816 (2015), Chang, S. et al. Emulsion-based Encapsulation of Pluripotent Stem Cells in Hydrogel Microspheres for Cardiac Differentiation. *Biotechnol. Prog.* btpr.2986 (2020) doi:10.1002/btpr.2986; Zhao, S. et al. Bioengineering of injectable encapsulated aggregates of pluripotent stem cells for therapy of myocardial infarction. *Nat. Commun.* 7, 1-12 (2016)).

Finally, it is known that cell retention after delivery in the heart of cardiomyocytes is very poor (Hou, D. et al. Radiolabeled cell distribution after intramyocardial, intracoronary, and interstitial retrograde coronary venous delivery: Implications for current clinical trials. *Circulation* 112, 150-156 (2005), which limits the effectiveness of cardiac cell therapy. In addition, during the grafting of cardiomyocytes as currently obtained, to regenerate cardiac tissues, there is a major risk of inducing an arrhythmia to the patient, which again limits the use of cell therapy for treating heart disease. In fact, to date, one of the most crucial scientific challenges to overcome in order to ensure the safety of stem cell derived cardiac cells for therapeutic applications related to cardiac diseases is the elimination of transplant arrhythmia induced during grafting (Menasché, P. Cardiac cell therapy: Current status, challenges and perspectives. *Archives of Cardiovascular Diseases* 113, 285-292 (2020); Kadota, S., Tanaka, Y. & Shiba, Y. Heart regeneration using pluripotent stem cells. *Journal of Cardiology* (2020) doi:10.1016/j.jjcc.2020.03.013; Chen, K., Huang, Y., Singh, R. & Wang, Z. Z. Arrhythmogenic risks of stem cell replacement therapy for cardiovascular diseases. *Journal of Cellular Physiology* (2020) doi:10.1002/jcp.29554). Although generally transient, arrhythmias were observed both in pigs (Romagnuolo, R. et al. Human Embryonic Stem Cell-Derived Cardiomyocytes Regenerate the Infarcted Pig Heart but Induce Ventricular Tachyarrhythmias. *Stem Cell Reports* 12, 967-981 (2019)) and non-human primates (Ichimua, h. et al. Allogeneic transplantation of iPS cell-derived cardiomyocytes regenerates primate hearts. *Nature* 538, 388-391 (2016); Liu, Y.-W. et al. Human embryonic stem cell-derived cardiomyocytes restore function in infarcted hearts of non-human primates. *Nature biotechnology* 36, 597-605 (2018); Chong, J. J. H. et al. Human embryonic-stem-cell-derived cardiomyocytes regenerate non-human primate hearts. *Nature* 510, 273-277 (2014)), large animal regeneration models after myocardial infarction.

There is therefore an important need for a solution for the large-scale production of quality cardiomyocytes, in order to meet an essential cardiac cell therapy demand, but also in the research and development of drug molecules to judge their efficacy and toxicity in the preclinical phase, before exposing patients to these treatments.

The objective of the invention is therefore to meet all of these needs and to overcome the disadvantages and limits of the prior art.

SUMMARY OF THE INVENTION

To meet this objective, the invention proposes to pass through a key developmental intermediate to obtain compacted tissues of human cardiac cells with particular characteristics and in large quantities, suitable for uses in cellular therapy.

For this purpose, the object of the invention is a three-dimensional (3D) cellular microcompartment comprising successively, organized around at least one lumen:

at least one inner layer of human cells undergoing cardiac differentiation, expressing at least one gene chosen from PDGFRα, MESP-1, NKX2-5, GATA4, MEF2C, TBX20, ISL1, and TBX5, said inner layer having a variable thickness;

at least one intermediate layer of isotonic aqueous solution, and at least one outer hydrogel layer.

Within the microcompartment, the inner layer of human cells and the lumen(s) together form a three-dimensional cellular object. If the smallest and largest thickness of the inner cell layer are measured along a segment passing through the geometric center of this cellular object, the ratio between the largest thickness and the smallest thickness is greater than or equal to 2. The inner layer thicknesses are measured along the segment passing through the geometric center of the cellular object:

a. between:
the interface of the inner layer and of the intermediate layer, and
the interface of the inner layer and of a lumen, and/or b. between:
the interface of the inner layer and of a lumen, and
the interface of the inner layer and of another lumen.

The specific object of the invention is therefore a cellular microcompartment comprising successively, organized around at least one lumen:

at least one inner layer of human cells undergoing cardiac differentiation, expressing at least one gene chosen from PDGFRα, MESP-1, NKX2-5, GATA4, MEF2C, TBX20, ISL1 and TBX5, said inner layer having a variable thickness, the ratio between the largest thickness and the smallest thickness of the inner layer being greater than or equal to 2, the smallest thickness and the largest thickness of the inner layer being the smallest and the largest of the inner layer thicknesses measured along a segment passing through the geometric center of the cellular object formed by the inner layer and the lumen(s), between the interface of the inner layer and intermediate layer and the interface of the inner layer and of a lumen, and/or between the interface of the inner layer and a lumen and the interface of the inner layer and another lumen, at least one intermediate layer of isotonic aqueous solution, and at least one outer hydrogel layer.

The microcompartment according to the invention therefore comprises cells undergoing cell differentiation, the expression of the genes PDGFRα/MESP1/NKX2-5/GATA4/MEF2C/TBX20/ISL1/TBX5 being associated with intermediate stages of cardiac differentiation. Such a configuration (one or more lumens around which are successively organized a layer of human cells undergoing cardiac differentiation with specific thickness characteristics, an isotonic aqueous solution layer, and at least one hydrogel layer) is novel. Indeed, there are several known protocols for differentiating hPSCs into cardiomyocytes which rely partially or totally on the modulation of the WNT pathway (Wingless and Int-1) (Dunn, K. K. & Palecek, S. P. Engineering scalable manufacturing of high-quality stem cell-derived cardiomyocytes for cardiac tissue repair. *Front. Med.* 5, (2018)). During hPSC directed cardiac differentiation, the cells undergo morphological changes during their transition to mesoderm, cardiac mesoderm, cardiac progenitors and finally to cardiac myocytes. In 2D culture of hPSC, these changes are known to be associated with distinct morphologies (Palpant, N. J. et al. Generating high-purity cardiac and endothelial derivatives from patterned meso- derm using human pluripotent stem cells. *Nat. Protoc.* 12, 15-31 (2017)). These morphological changes have not been well-described in a 3D culture system and the topology of the object of the invention has never been obtained and described. However, advantageously, this topology makes it possible to then obtain compacted tissues in large numbers and having characteristics that enable their use to regenerate damaged cardiac tissues.

The presence of an outer hydrogel layer and an interme- diate layer of isotonic aqueous solution allows uniform distribution of the cells between the microcompartments. Thus, the homogeneity between the microcompartments is greatly improved by the prior encapsulation of the hPSCs, allowing for increased yield and quality compared with existing methods. Moreover, this hydrogel layer makes it possible to avoid microcompartment fusions, which are a major source of variability unfavorable for phenotypic homogeneity and the survival of cardiac cells produced in a bioreactor.

In addition, modulation of the WNT pathway used in cardiac differentiation is associated with β-catenin degrada- tion (Lam, A. T. L. et al. Conjoint propagation and differ- entiation of human embryonic stem cells to cardiomyocytes in a defined microcarrier spinner culture. *Stem Cell Res. Ther.* 5, 1-15 (2014)), a molecule that plays a role in cell-cell adhesion complexes (Brembeck, F. H., Rosario, M. & Birch- meier, W. Balancing cell adhesion and Wnt signaling, the key role of β-catenin. *Curr. Opin. Genet. Dev.* 16, 51-59 (2006)). Advantageously, the topology of the microcompart- ment according to the invention makes it possible to protect the cells undergoing cardiac differentiation, despite the fragility of the cell-cell adhesion induced by modulation of the WNT pathway.

The microcompartments according to the invention can be used to obtain compacted tissues of specific differentiated human cardiac cells. The invention therefore also relates to the use of a cellular microcompartment according to the invention, to obtain a heart cell tissue expressing cardiac troponin C and preferentially also alpha-actinin.

The invention therefore also relates to compacted cardiac tissues. In particular, the invention relates to a compacted tissue of human cardiac cells expressing cardiac troponin C (that is human cells expressing the gene of cardiac troponin C, the alias of the corresponding gene being TNNC1), obtained from at least one cellular microcompartment as previously described, by a method comprising the compact- ing of the inner layer of human cells by total or partial disappearance of the lumen(s). Preferentially, the compacted cardiac cell according to the invention has a level of cells expressing cardiac troponin C of at least 50% by number relative to the total number of cells constituting the com- pacted tissue, even more preferentially at least 60%, at least 70%, at least 75%, at least 80%, and this level may be greater than 90%. Preferentially, the compacted cardiac cell according to the invention has a level of cells expressing alpha-actinin of at least 50% by number relative to the total number of cells constituting the compacted tissue, even more preferentially at least 60%, at least 70%, at least 75%, at least 80%, and this level may be greater than 90%. Preferentially, the compacted cardiac cell according to the invention has a level of cells expressing troponin C and alpha-actinin of at least 50% by number relative to the total number of cells constituting the compacted tissue, even more preferentially at least 60%, at least 70%, at least 75%, at least 80%, and this level may be greater than 90%.

In the prior art, it has been described in Jing Donghui et al. *"Cardiac cell generation from encapsulated embryonic stem cells in static and scalable culture systems"*, Cell *Transplantation*, col. 19, no 11, 1 Nov. 2010, pages 1397- 1492 cardiac tissues obtained by encapsulating mouse or human ESCs in alginate beads coated with polylysine, then dissolving the nucleus by incubation in a sodium citrate solution. This solution, demonstrated from embryonic stem cells, is not satisfactory, as the purity of the obtained tissue, and in particular the level of cells expressing cardiac tro- ponin C is less than 20%, which is not sufficient to consider use in therapy. Moreover, having too many cellular impu- rities in tissues poses a risk to the patient by introducing undesired cells into the cardiac muscle, which could disrupt its proper functioning, in particular by disrupting its elec- trical conductivity and/or its contraction capacity. In addi- tion, the use of polylysine in the concentrations described in this article has a risk of toxicity to the cells.

Likewise in Koivisto Janne T. et al. "Mechanically Bio- mimetic Gelatin-Gellan Gum Hydrogels for 3D Culture of Beating Human Cardiocytes", Applied Materials & Inter- faces, vol. 11, no. 23, 12 Jun. 2019, pages 20589-20602, the encapsulation of cells within a hydrogel without space available for the organisation of the cells, presumably after cell proliferation, which mechanically pressurises the hydro- gel is described. There is no encapsulation in microcom- partments and this does not lead to a suitable contractile frequency, nor to a level of cells expressing cardiac troponin C sufficient for use in therapy.

Heart tissues according to the invention, obtained by a specific method different from those of the prior art, make it possible to obtain heart tissues with a level of cells express- ing cardiac troponin C and/or alpha-actinin of at least 50%, and preferentially at least 75%. Indeed, the configuration according to the invention during differentiation allows the transmission of auto/paracrine signals within a protected lumen, which allows the cells to self-organize the structure in vivo in a biomimetic manner. This structure is extremely fragile and requires both mechanical protection and space available contrary to what is described in Koivisto Janne T et al. According to the invention, this configuration cannot be put into place or in a confined system, nor in an unprotected system. In fact, cardiac differentiation is not very reproducible in vitro in conventional systems (both 3D and 2D, https://www.sciencedirect.com/science/article/pii/ S2213671118301504) which results in incomplete control of the cellular environment. In a non-obvious and surprising manner, the invention proposes controlled structuring of the environment in the form of a protected self-organization, which allows less sensitivity to small variations in the culture system and therefore greater reproducibility.

Heart tissues according to the invention can be used to regenerate ischemic cardiac tissues. Thus, the invention relates to said tissues for their use in the prevention and/or treatment of pathologies, in particular heart disease.

Other features and advantages will emerge from the detailed description of the invention and the following examples.

BRIEF DESCRIPTION OF THE FIGURES

FIG. 1b is a phase-contrast microscopy image of a micro-compartment according to the invention taken at 4× magnification, which corresponds to the schematic diagram of FIG. 1a.

FIG. 2b is a phase-contrast microscopy image of a micro-compartment according to the invention taken at 4× magnification, which corresponds to the schematic diagram of FIG. 2a.

FIG. 3b is a phase-contrast microscopy image of a micro-compartment according to the invention taken at 4× magnification, which corresponds to the schematic diagram of FIG. 3a.

FIG. 4b is a phase-contrast microscopy image of a compacted tissue according to the invention in a microcompartment taken at 4× magnification, which corresponds to the schematic diagram of FIG. 4a.

DETAILED DESCRIPTION OF THE INVENTION

Definitions

Figure 1A:
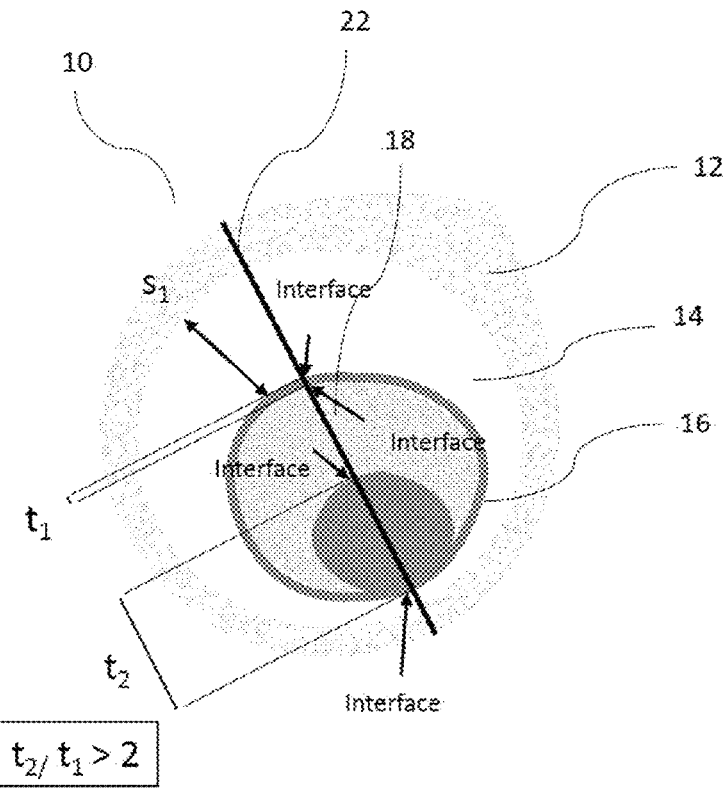
FIG. 1*a* is a schematic representation of a sectional view of a cellular microcompartment 10 according to the inven- tion, corresponding to the photo shown in FIG. 1*b*, with an outer hydrogel layer 12, a layer of isotonic aqueous solution 14, a layer of human cells undergoing cardiac differentiation 16 with a larger thickness t2 and a smaller thickness t1, and an internal lumen 18.

For the purposes of the invention, the term "alginate" means linear polysaccharides formed from β-D-mannuronate and α-L-guluronate, salts and derivatives thereof.

Within the meaning of the invention, "hydrogel capsule" means a three-dimensional structure formed from a matrix of polymer chains, inflated with a liquid and preferentially water.

Cell "expressing a gene" within the meaning of the invention means a cell which contains at least 5 times more copies of the RNA transcribed from the DNA sequence of the gene concerned in comparison with a pluripotent cell, preferentially 10 times more copies, preferentially 20 times more copies, preferentially 100 times more copies.

Within the meaning of the invention, "human cells" means human cells or immunologically humanized non-human mammalian cells. Even when this is not specified, the cells, stem cells, progenitor cells and tissues according to the invention are constituted or are obtained from human cells or from immunologically humanized non-human mammalian cells.

Within the meaning of the invention, "progenitor cell" means a stem cell already engaged in cardiac differentiation but not yet differentiated.

Within the meaning of the invention, "embryonic stem cell" means a pluripotent stem cell derived from the internal cell mass of the blastocyst. The plural of the embryonic stem cells can be evaluated by the presence of markers such as transcription factors OCT4, NANOG and SOX2 and surface markers such as SSEA3/4, Tra-1-60 and Tra-1-81. The embryonic stem cells used in the context of the invention are obtained without destruction of the embryo from which they come, for example using the technique described in Chang et al. (Cell Stem Cell, 2008, 2(2)): 113-117). Optionally, embryonic stem cells of human beings can be excluded.

"Pluripotent stem cell" or "pluripotent cell" within the meaning of the invention means a cell which has the capacity to form all the tissues present in the organism that are originally whole, without however being able to form an entire organism as such. Human pluripotent stem cells can be called hPSC in the present application. It may in particular be induced pluripotent stem cells (iPSC or hiPSC for human induced pluripotent stem cells), embryonic stem cells or MUSE cells (for "Multilineage-differentiating Stress Enduring" cells).

Within the meaning of the invention, "induced pluripotent stem cell" is intended to mean a pluripotent stem cell induced to pluripotence by genetic reprogramming of differentiated somatic cells. These cells are in particular positive for pluripotence markers, such as staining with alkaline phosphatase and the expression of the proteins NANOG, SOX2, OCT4 and SSEA3/4. Examples of methods for obtaining induced pluripotent stem cells are described in the articles Yu et al. (Science 2007, 318 (5858): 1917-1920), Takahashi et al (Cell, 207, 131(5): 861-872) and Nakagawa et al (Nat Biotechnol, 2008, 26(1): 101-106).

Within the meaning of the invention, "differentiated cardiac cells" means cells which have the phenotype of a cardiomyocyte, that is, expressing specific markers such as TNNC1 (cardiac troponin C gene) and ACTN2 (alpha actinin gene) and capable of spontaneously contracting in response to a spontaneous intracellular calcium signal (in the case of immature cardiac cells) or following an electrical or chemical stimulation capable of triggering said calcium signal.

Within the meaning of the invention, "differentiated" cells means cells which have a particular phenotype, as opposed to pluripotent stem cells which are not differentiated.

"Feret diameter" of a compacted cardiac tissue according to the invention or of a microcompartment according to the invention means the distance "d" between two tangents to said compacted tissue or to said microcompartment, these two tangents being parallel, such that the entire projection of said compacted tissue or of said microcompartment is comprised between these two parallel tangents.

Within the meaning of the invention, "variable thickness" of the inner layer of human cells undergoing differentiation is understood to mean that the inner layer in the same microcompartment does not have the same thickness throughout.

Within the meaning of the invention, "implantation" or "graft" in the heart means the action of depositing in the heart at a particular location at least one compacted tissue according to the invention. The implantation can be carried out by any means in particular by injection.

Within the meaning of the invention, "microcompartment" or capsule" means a three-dimensional or totally enclosed structure containing at least one cell.

Within the meaning of the invention, "convective culture medium" means a culture medium animated by internal movements.

Within the meaning of the invention, "largest dimension" of a compacted cardiac tissue according to the invention or of a microcompartment according to the invention means the value of the largest Feret diameter of said compacted tissue or of said microcompartment.

Within the meaning of the invention, "smallest dimension" of a compacted cardiac tissue according to the invention or of a microcompartment according to the invention means the value of the smallest Feret diameter of said compacted tissue or of said microcompartment.

Within the meaning of the invention, "tissue" or "biological tissue" has the common meaning of tissue in biology, that is the intermediate organizational level between the cell and the organ. A tissue is a set of similar cells of the same origin (most often derived from a common cellular line, although they can find originate through association of distinct cellular lines), grouped in clumps, networks, or bundles (fibers). A tissue forms a functional assembly, that is to say that its cells contribute to the same function. Biological tissues regenerate regularly and are assembled together to form organs.

Within the meaning of the invention, "compacted cardiac tissue" or "compacted tissue of cardiac cells" means a unit of tissue comprising at least one cardiac tissue consisting at least of differentiated cardiac cells. The tissue is at least partially compacted, that is it is composed mainly of cells, in particular its volume is composed of more than 50% of cells, preferentially 75% of cells, preferentially 90% of cells. The tissue can be fully compacted, that is the lumens are no longer detectable and/or there are no lumens. The compacted tissues according to the invention can be called microtissues.

Within the meaning of the invention, "lumen" means a volume of aqueous solution topologically surrounded by cells. Preferentially, its content is not in diffusive equilibrium with the volume of convective liquid present outside the microcompartment.

Cellular Microcompartments

The object of the invention is a cellular microcompartment comprising successively, organized around at least one lumen:

at least one inner layer of human cells undergoing cardiac differentiation, expressing at least one gene chosen from PDGFRα, MESP-1, NKX2-5, GATA4, MEF2C, TBX20, ISL1, and TBX5, said inner layer having a variable thickness (called "inner layer"), at least one intermediate layer of isotonic aqueous solution (called "intermediate layer"), and at least one outer hydrogel layer (called "outer layer").

The microcompartment according to the invention is a three-dimensional structure therefore comprising at least one inner layer of cells. These cells are living human cells, undergoing cardiac differentiation. This layer of cells is organized in three dimensions in the microcompartment.

Human cells undergoing cardiac differentiation in the microcompartment are cells expressing at least one gene chosen from PDGFRα, MESP-1, NKX2-5, GATA4, MEF2C, TBX20, ISL1 and TBX5. These genes are specific to cardiac cells undergoing differentiation. Preferentially, the human cells undergoing cardiac differentiation present in the microcompartment express at least two of these genes. According to one variant, the human cells undergoing cardiac differentiation present in the microcompartment express all these genes.

Figure 2A:
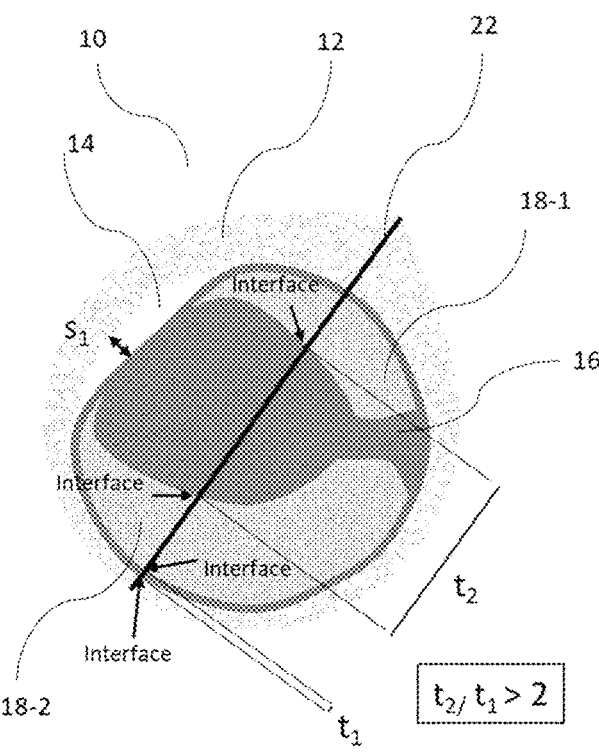
FIG. 2a is a schematic representation of a sectional view of a cellular microcompartment 10 according to the invention, corresponding to the photo shown in FIG. 2b, with an outer hydrogel layer 12, a layer of isotonic aqueous solution 14, a layer of human cells undergoing cardiac differentiation 16 with a larger thickness t2 and a smaller thickness t1, and two internal lumens 18-1 and 18-2, S1 representing the thickness of the layer of isotonic aqueous solution 14.
Figure 3A:
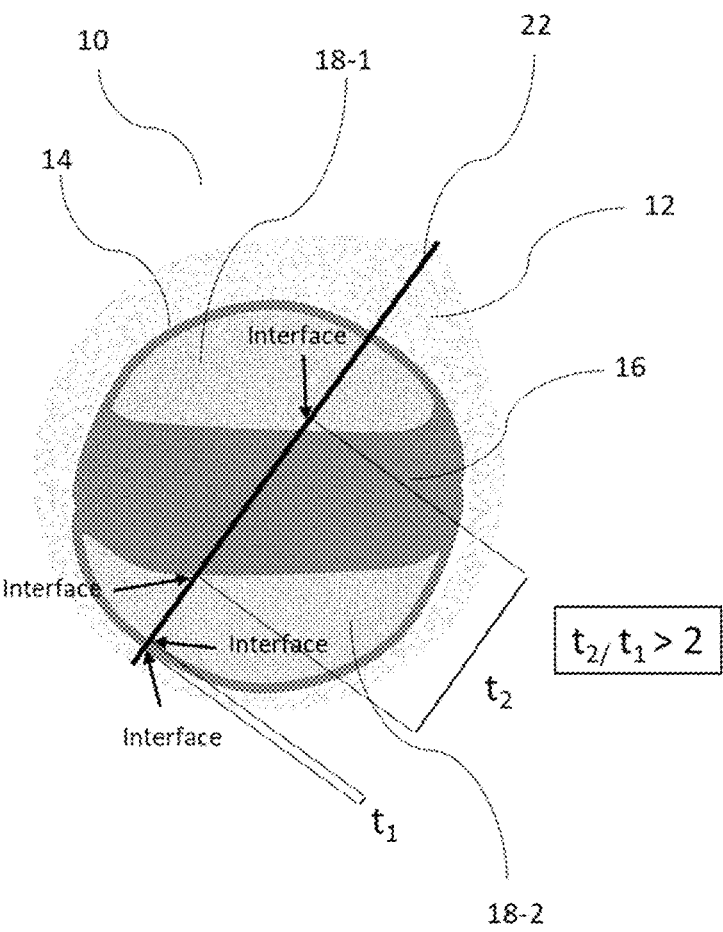
FIG. 3a is a schematic representation of a sectional view of a cellular microcompartment 10 according to the invention, corresponding to the photograph shown in FIG. 3b, with an outer hydrogel layer 12, a layer of isotonic aqueous solution 14, a layer of human cells undergoing cardiac differentiation 16 with a larger thickness t2 and a smaller thickness t1, and two internal lumens 18-1 and 18-1, s1 representing the thickness of the layer of isotonic aqueous solution 14.

The inner layer of human cells undergoing cardiac differentiation has a variable thickness. Within the microcompartment, the inner layer of human cells and the lumen(s) together form a three-dimensional cellular object. If the smallest and largest thickness of the inner cell layer are measured along a segment passing through the geometric center of this cellular object (shown as 22 in FIGS. 1*a*, 2*a*, and 3*a*), the ratio between the largest thickness and the smallest thickness is greater than or equal to 2, preferentially greater than or equal to 5. The inner layer thicknesses are measured along the segment passing through the geometric center of the cellular object:

a. between:

the interface of the inner layer and of the intermediate layer, and the interface of the inner layer and of a lumen, and/or b. between:

the interface of the inner layer and of a lumen, and the interface of the inner layer and of another lumen.

FIGS. 1, 2 and 3 show examples of cellular microcompartments 10 according to the invention, with an outer hydrogel layer 12, an isotonic aqueous solution layer 14, one or more internal lumen(s) 18, 18-1, 18-2, a layer of human cells undergoing cardiac differentiation 16 with a larger thickness t2 and a smaller thickness t1 (the thicknesses being measured along a segment 22 passing through the geometric center of this cellular object formed by the layer 16 and the lumen(s) 18, 18-1, 18-2), the ratio t2/t1 being much greater than 2.

In FIG. 1, there is only one slot 18 and consequently the inner layer thicknesses are measured along a segment 22 passing through the geometric center of the cellular object formed by the layer 16 and the lumen 18, between the interface of the inner layer and of the intermediate layer and the interface of the inner layer and of the lumen 18.

In FIGS. 2 and 3, there are two lumens 18-1 and 18-2, and therefore the inner layer thicknesses are measured along a segment 22 passing through the geometric center of the cellular object formed by the layer 16 and the lumens 181-18-2:

between the interface of the inner layer and the intermediate layer and the interface of the inner layer and of the lumen 18-1, and between the interface of the inner layer and the intermediate layer and the interface of the inner layer and of the lumen 18-2, and between the interface of the inner layer and the lumen 18-1 and the interface of the inner layer and of the lumen 18-2.

The number of human cells undergoing cardiac differentiation in the inner layer is preferentially between 1 and 100,000 cells, even more preferentially between 50 and 50,000 cells, and especially between 500 and 25,000 cells.

The human cells undergoing cardiac differentiation in the inner layer were preferentially obtained from pluripotent stem cells, in particular from human pluripotent stem cells, or optionally from non-pluripotent human cells whose transcriptional profile was artificially modified to attain that of cardiac progenitors or cardiac cells, typically by forced expression of specific target cell phenotype transcription factors. Preferentially, the human cells in the inner layer were obtained from human pluripotent stem cells after being placed in contact with a solution capable of initiating differentiation of said stem cells.

The intermediate layer of isotonic aqueous solution preferentially contains peptide or peptidomimetic sequences capable of binding to integrins. "Isotonic aqueous solution" means an aqueous solution having an osmolarity of between 200 and 400 mOsm/L. This layer is located between the inner layer of cells and the outer hydrogel layer.

The intermediate layer may consist of elements which have been added during the manufacture of the microcompartment and/or of elements added to the microcompartment and/or of elements secreted or induced by the other constituents of the microcompartment.

The intermediate layer may in particular comprise or consist of an extracellular matrix and/or a culture medium. If it comprises an extracellular matrix, it may be an extracellular matrix secreted by cells of the inner layer and/or by the extracellular matrix added when the microcompartment was prepared/fabricated.

The intermediate layer preferentially comprises a mixture of proteins and extracellular compounds required for culturing the cells undergoing cardiac differentiation. Preferentially, the intermediate layer comprises structural proteins, such as collagen, laminins, enactin, vitronectin, and growth factors, such as TGF-beta and/or EGF. According to one variant, the intermediate layer may consist of or comprise Matrigel® and/or Geltrex® and/or a matrix of a hydrogel type of plant origin such as modified alginates or of synthetic origin or copolymer of poly(N-isopropylacrylamide) and poly(ethylene glycol) (PNIPAAm-PEG) like Mebiol®.

According to one variant, the intermediate layer may form a gel.

At the surface of the intermediate layer in contact with the inner layer of human cells undergoing differentiation, the intermediate layer may optionally contain one or more cells.

The thickness of the intermediate layer (designated s1 in FIGS. 1 and 2) is preferentially between 30 nm and 300 μm, even more preferentially between 30 nm and 50 μm.

The presence of the intermediate layer promotes the structuring, according to the invention, of elements in the microcompartment.

The microcompartment and the inner layer of cells within the microcompartment according to the invention are hollow. Indeed, the microcompartment according to the invention always comprises at least one internal lumen which constitutes the hollow part of the microcompartment. The lumen contains a liquid, in particular a culture medium (such as for example a basal RPMI medium with a B27 supplement) and/or a liquid secreted by the cells of the inner layer. Advantageously, the presence of this hollow part allows the cells to have a small diffusive volume whose composition they can control, promoting a so-called autocrine/paracrine cell communication which is in turn favorable to cardiac differentiation.

According to one embodiment, as shown in FIGS. 2 and 3, the microcompartment according to the invention can comprise a plurality of lumens, at least two lumens. This situation has the same advantage with respect to autocrine and paracrine signals as the presence of a single lumen, and increases the cells' ability to control the composition of the aqueous solution of the lumen, since the cell to volume/cells ratio is thereby geometrically lower. Furthermore, the stabilization of such a configuration demonstrates the mechanical protection offered by the microcompartment.

The lumen(s) represent (s) preferentially between 10% and 90% of the volume of the microcompartment according to the invention.

The microcompartment comprises an outer hydrogel layer. Preferentially, the hydrogel used is biocompatible, that is it is not toxic to the cells. The hydrogel layer must allow the diffusion of oxygen and nutrient to supply the cells contained in the microcompartment and allow their survival. According to one embodiment, the outer hydrogel layer comprises at least alginate. It may consist exclusively of alginate. The alginate can in particular be a sodium alginate, composed of 80% α-L-guluronate and 20% β-D-mannuronate, with an average molecular weight of 100 to 400 kDa and a total concentration of between 0.5 and 5% by mass.

The hydrogel layer protects the cells from the external environment, limits uncontrolled proliferation of the cells, and allows their controlled differentiation into cells undergoing cardiac differentiation and then into cardiac cells, at least into cardiomyocytes.

The outer layer is closed or partially closed. The microcompartment is therefore closed or partially closed. Preferentially, the microcompartment is closed.

The microcompartment according to the invention can be in any three-dimensional form, that is, it may have the shape of any object in space. Preferentially, the microcompartment according to the invention is in spherical or elongated form. It may in particular be in the form of a hollow spheroid, a hollow ovoid, a hollow cylinder or a hollow sphere.

It is the outer layer of the microcompartment, that is the hydrogel layer, which imparts its size and shape to the microcompartment according to the invention. Preferentially, the smallest dimension of the microcompartment according to the invention is between 10 μm and 1 mm, preferentially between 100 μm and 700 μm. It may be between 10 μm and 600 μm, in particular between 10 μm and 500 μm. This smallest dimension is important for the survival of the three-dimensional cardiac tissue that will be obtained from the microcompartment according to the invention, in particular to promote the survival of cardiac cells within cardiac tissue and optimize the reorganization and vascularization of cardiac tissue after implantation in the heart.

Its largest dimension is preferentially greater than 10 μm, more preferentially between 10 μm and 1 m, even more preferentially between 10 μm and 50 cm. According to one embodiment, the largest dimension is compatible with the size of the member and is therefore less than 30 cm (between 10 μm and 30 cm).

The microcompartment according to the invention is particularly useful for obtaining a three-dimensional compacted cardiac tissue, consisting of differentiated human cardiac cells.

The microcompartment according to the invention may optionally be frozen to be stored. It must then be thawed in order to continue the maturation of the cardiac cells and obtain a three-dimensional compacted cardiac tissue.

The invention also relates to a plurality of microcompartments together. Thus, the invention also relates to a series of cellular microcompartments as described above comprising at least two cellular microcompartments according to the invention. Preferentially, the series of microcompartments according to the invention is in a culture medium, in particular in an at least partially convective culture medium. According to a particularly suitable embodiment, the object of the invention is a series of cellular microcompartments as described above in a closed chamber, such as a bioreactor, preferentially in a culture medium in a closed chamber, such as a bioreactor.

Method for Obtaining a Microcompartment According to the Invention

The invention also relates to a method for preparing a microcompartment according to the invention.

In particular, the method consists of producing cellular microcompartments comprising a hydrogel capsule surrounding:

stem cells or progenitor cells capable of differentiating into cardiac cells, at least into cardiomyocytes, or
    differentiated cells intended to undergo reprogramming within the capsule so that they become induced pluripotent stem cells capable of differentiating into cardiac cells, at least into cardiomyocytes.

The method for preparing a microcompartment according to the invention may comprise at least the implementation of the steps which consist of:

producing a cellular microcompartment comprising, within a hydrogel capsule:
    elements of isotonic aqueous solution, preferentially of extracellular matrix, secreted by the cells or supplied by the operator, preferentially at least part of the isotonic aqueous solution being provided in addition to the extracellular matrix naturally secreted by the cells,
    cells capable of differentiating into cardiac cells,
    inducing cellular differentiation within the cellular microcompartment, so as to obtain at least one hollow three-dimensional layer of human cells undergoing cardiac differentiation, expressing at least one gene chosen from PDGFRα, MESP-1, NKX2-5, GATA4, MEF2C, TBX20, ISL1 and TBX5, and optionally other cells.

Advantageously, the total or partial encapsulation in the hydrogel and the combined addition of extracellular matrix is a means suitable for allowing the differentiation of human pluripotent cells to the cardiac muscle combining several advantages, in particular:

i) promoting homogeneous distribution of the cells of the batch within the microcompartments,
    ii) mechanical protection against hydrodynamic stresses inflicted by the bioreactor and limiting undesired fusions of microcompartments,
    iii) organization of a microenvironment locally retaining the extracellular matrix elements that promote good survival and good cell organization,
    iv) maintaining a lumen promoting the autocrine and paracrine pathways during differentiation.

Any method for producing cellular microcompartments containing inside a hydrogel capsule at least human cells undergoing cardiac differentiation and an isotonic aqueous solution and optionally adding other cells, for example support cells, may be used. A suitable method is notably described in application WO 2018/096277. Preferentially the encapsulation is carried out by co-injection of three solutions:

a hydrogel solution,
    an isotonic intermediate solution such as for example a sorbitol solution,
    a solution comprising the cells to be encapsulated, the culture medium, and optionally but preferentially the extracellular matrix,
    concentrically via a microfluidic injector which makes it possible to form a jet at the outlet of the injector consisting of the mixture of the three solutions, said jet splitting into drops, said drops being collected in a calcium bath which stiffens the hydrogel solution to form the outer layer of each microcompartment, the inner part of each drop being constituted by the solution comprising the encapsulated cells, the culture medium and the extracellular matrix.

According to one embodiment, the encapsulation is carried out with a device capable of generating hydrogel capsules using a microfluidic chip. For example, the device may comprise syringe shoots for several solutions injected concentrically thanks to a microfluidic injector which makes it possible to form a jet which is divided into drops that are then collected in a calcium bath. According to a particularly suitable embodiment, three solutions are loaded on three syringe pumps:

a hydrogel solution, for example alginate, an isotonic intermediate solution such as for example a sorbitol solution, the solution derived from step b) comprising iPSCs, culture medium, and optionally but preferentially extracellular matrix.

The three solutions are co-injected (simultaneously injected) concentrically using a microfluidic or microfluidic chip injector which makes it possible to form a jet that splits into drops whose outer layer is the hydrogel solution and the core of the solution comprising the cells to be encapsulated; these drops are collected in a calcium bath which stiffens the alginate solution to form the shell.

To improve the monodispersity of the cellular microcompartments, the hydrogel solution is charged with a direct current. A grounding ring is arranged after the tip in the plane perpendicular to the axis of the jet exiting from the microfluidic injector (coextrusion chip) to generate the electrical field.

In a particular embodiment, the step of producing a cellular microcompartment of the preparation method according to the invention comprises the steps consisting of:

incubating pluripotent stem cells in a culture medium, preferentially a culture medium containing the growth factors FGF2 and TGFβ or molecules reproducing its action on the cell, an inhibitor of the Rho kinase pathway or a molecule reproducing its action on the cell, in particular by limiting cell death.

optionally mixing the pluripotent stem cells with an isotonic aqueous solution, preferentially an extracellular matrix, encapsulating the mixture into a hydrogel layer.

The cells encapsulated for the preparation of microcompartments according to the invention are preferentially chosen from:

cells capable of differentiating at least into cardiac cells, these cells being:

either stem cells capable of differentiating into cardiac cells, at least into cardiomyocytes, preferentially embryonic stem cells or induced pluripotent stem cells, very preferentially induced pluripotent stem cells, and/or or progenitor cells capable of differentiating into cardiac cells, at least into cardiomyocytes, and/or differentiated cells capable of undergoing reprogramming so that they become induced pluripotent stem cells capable of differentiating into cardiac cells, at least into cardiomyocytes.

The encapsulated cells can be immuno-compatible with the person intended to receive the differentiated cardiac cells obtained from the microcompartment according to the invention, to avoid any risk of rejection. In one embodiment, the encapsulated cells were previously taken from the person in whom the compacted cardiac tissues obtained from the microcompartments according to the invention will be implanted.

The differentiation into cells undergoing cardiac differentiation contained in the microcompartment according to the invention can be carried out by any suitable method. It may in particular be a known method as one of the protocols listed in Dunn, K K & Palecek, S P "Engineering fabrication évolutive de cardiomyocytes dérivés de cellules souches de haute qualité pour la réparation des tissus cardiaques." Front. Med. 5, (2018)).

The protocol which is currently one of the most common is described in detail in (Burridge, P. W. et al. Chemically defined generation of human cardiomyocytes. Nat. Methods 11, 855-860 (2014)).

In a particular embodiment, the step of inducing cell differentiation of the method according to the invention comprises a step consisting of introducing capsules containing human stem cells capable of being differentiated into human cardiac cells, in a culture medium containing a WNT pathway activator (such as CHIR99021) for 12 h to 72 h, more preferentially 12 to 48 hours.

Next, the process may comprise a step which consists of incubating the microcompartments in a culture medium containing an inhibitor of the WNT pathway. Preferentially, this step is carried out between 0 and three days after the end of the step of inducing differentiation (addition of the activator of the WNT pathway), preferentially between 12 and 72 hours, in particular between 24 and 48 h. According to a preferred embodiment, this step consists of incubating the capsules in a culture medium containing an inhibitor of the WNT pathway, preferentially for 12 hours to 48 hours, in particular between 24 and 48 h.

One particular embodiment is as follows:

(a) incubating human pluripotent stem cells containing capsules in a culture medium containing a WNT pathway activator for 12 h to 72 h;

(b) 0 to 48 hours after step (a) incubating the capsules in a culture medium containing a WNT pathway inhibitor for 12 hours to 48 hours;

Preferentially, the culture medium is RPMI with B27 supplement without insulin (during the first 7 days of differentiation) and with insulin (from the day of differentiation 7).

Preferentially, the microcompartments according to the invention, containing cells undergoing cardiac differentiation, are obtained between 2 to 7 days after the beginning of the induction of differentiation, preferentially between 3 and 7 days after the start of inducing differentiation, even more preferentially between 4 and 6 days after the start of differentiation. Preferentially, the microcompartment according to the invention appears at the moment when the WNT pathway inhibitor is added, or after.

The lumen is generated at the time of the formation of the layer of human cells undergoing cardiac differentiation in 3 dimensions, by the cells that multiply and develop. The lumen can contain a liquid and in particular the culture medium used for the implementation of the method.

According to one embodiment, the initial stem cells are organized into a layer of stem cells in three dimensions around a lumen in the microcompartment, then during differentiation this lumen disappears, and a second lumen appears to form the microcompartment according to the invention.

The method is preferentially implemented in a closed chamber, such as a bioreactor, with a series of microcompartments, even more preferentially in a suitable culture medium that is at least partially convective.

The method according to the invention may optionally also comprise:

a step which consists of dissociating the microcompartment or the series of microcompartments in order to obtain a suspension of cells or a suspension of cell clusters; the removal of the capsule can be carried out in particular by hydrolysis, dissolution, drilling and/or rupture by any means that is biocompatible, that is non-toxic to the cells. For example, the removal may be accomplished using a phosphate buffer, a divalent ion chelator, an enzyme such as alginate lyase if the hydrogel comprises alginate and/or laser microdissection, and a step of re-encapsulating all or some of the cells or clusters of cells in a hydrogel capsule.

The re-encapsulation is a means adapted to:

i) optimize the standardization of the size and homogeneity of the compacted cardiac tissues that will then be obtained, ii) allow an increase in cell amplification obtained from the pluripotent step, and therefore a higher yield.

At any time, the method according to the invention may comprise a step consisting of verifying the phenotype of the cells contained in the microcompartment. This verification can be carried out by identifying the expression by at least some of the cells contained in the microcompartment, of at least one of the following genes: PDGFRα, MESP-1, NKX2-5, GATA4, MEF2C, TBX20, ISL1 and TBX5.

The method according to the invention may comprise a step of freezing the microcompartments according to the invention before their use to continue differentiation into differentiated cardiac cells and to obtain compacted cardiac tissues. The freezing is preferentially carried out at a temperature comprised between −190° C. and −80° C. The thawing can be carried out in a warm water bath (37 degrees preferentially) so that the cells thaw quite rapidly. The microcompartments according to the invention before they are used to continue differentiation into differentiated cardiac cells and obtain compacted cardiac tissues, can be maintained at more than 4° C. for a limited period of time before they are used, preferentially between 4° C. and 38° C.

The microcompartment according to the invention can also be used to continue differentiation into differentiated cardiac cells and to obtain compacted cardiac tissues, directly after implementation of the method according to the invention, without storage and without freezing.

Method for Obtaining Compacted Cardiac Tissue

After obtaining a microcompartment according to the invention containing human cells undergoing differentiation, the method can continue in order to obtain a three-dimensional object in the form of a compacted tissue.

The compacted object generally appears between 2 and 10 days after the addition of the inhibitor of the WNT pathway, in particular between 5 and 7 days. Indeed, the addition of the inhibitor is preliminary to the compacting of the cells which continue to differentiate into cardiac cells.

Thus, the compacted object generally appears between 7 and 14 days after the initiation of the differentiation.

At the end of compacting, all or some of the lumens have partially or totally disappeared (have been eliminated partially or totally by the compacting phenomenon) and the cells comprise at least in part cardiac human cells, preferentially at least cardiomyocytes.

The method according to the invention may comprise a step of amplifying cardiac cells in the microcompartment, and optionally one or more re-encapsulations.

The obtained compacted cardiac tissue can be maintained in the hydrogel capsule. Preferentially, it is always surrounded by an isotonic aqueous solution, preferentially an extracellular matrix. A capsule containing a three-dimensional compacted cardiac tissue and an isotonic aqueous solution layer is shown in FIG. 4.

The compacted tissue is preferentially stored in a capsule before use. For storage, the capsule containing the compacted cardiac tissue can be frozen before removing the hydrogel layer from the capsule. The method according to the invention can comprise a step of freezing the capsules containing the compacted cardiac tissues according to the invention before they are used. Freezing is preferentially carried out at a temperature of between −190° C. and −80° C. The capsules containing the compacted cardiac tissues according to the invention before they are used as grafts in the heart may be thawed in a warm water bath (37 degrees preferentially) so that the cells of the tissue thaw quite rapidly. The compacted cardiac tissues according to the invention can be kept at more than 4° C. for a limited period of time before their use, preferentially between 4° C. and 38° C.

After obtaining the compacted cardiac tissue, at any time before implantation in the heart, the method according to the invention may comprise a step consisting of verifying the phenotype of the cells contained in the capsule. This verification can be carried out by identifying the expression of cardiac troponin C by the cardiac cells forming the compacted tissue.

Preferentially, before use, the hydrogel layer of the capsule containing the compacted cardiac tissue according to the invention is removed. The removal of the capsule can be carried out in particular by hydrolysis, dissolution, drilling and/or rupture by any means that is biocompatible, that is non-toxic to the cells. For example, the removal may be accomplished using a phosphate buffer, a divalent ion chelator, an enzyme such as alginate lyase if the hydrogel comprises alginate and/or laser microdissection.

The removal of the hydrogel is preferentially total, the compacted cardiac tissue according to the invention is devoid of hydrogel when it is used as a graft, implanted in a heart.

Three-Dimensional Compacted Cardiac Tissue

The invention also relates to the cardiac tissue obtained according to the method as described above. The subject of the invention is therefore a compacted tissue of human cells expressing cardiac troponin C and preferentially alpha-actinin, obtained from at least one cellular microcompartment according to the invention.

In particular, the invention relates to a compacted tissue of human cells expressing cardiac troponin C, obtained from at least one cellular microcompartment according to the invention, by a method comprising the compaction (compaction known as secondary compaction) of the layer of human cells by total or partial disappearance of the lumen(s) of said microcompartment. Preferentially, the compacted heart cell tissue is obtained by a method as described above.

The tissue according to the invention is therefore a human tissue comprising at least differentiated cardiac cells expressing cardiac troponin C and preferentially alpha-actinin. The compacted tissue according to the invention can also contain other cell types.

Advantageously, the cardiac tissue according to the invention has a level of cells expressing cardiac troponin C of at least 50% by number relative to the total number of cells constituting the compacted tissue, even more preferentially at least 60%, at least 70%, at least 75%, at least 80%, at least 90%. This significant level of cells expressing cardiac troponin C is advantageous for envisaging uses of cardiac tissues according to the invention in cell therapy.

Preferentially, the compacted cardiac cell according to the invention has a level of cells expressing alpha-actinin of at least 50% by number relative to the total number of cells constituting the compacted tissue, even more preferentially at least 60%, at least 70%, at least 75%, at least 80%, and this level may be greater than 90%. This significant level of cells expressing alpha-actinin is advantageous for envisaging uses of cardiac tissues according to the invention in cell therapy.

Preferentially, the compacted cardiac cell according to the invention has a level of cells expressing troponin C and alpha-actinin of at least 50% by number relative to the total number of cells constituting the compacted tissue, even more preferentially at least 60%, at least 70%, at least 75%, at least 80%, and this level may be greater than 90%. This significant level of cells expressing both troponin C and alpha-actinin is advantageous for envisaging uses of cardiac tissues according to the invention in cell therapy.

Preferentially, this compacted tissue is contractile and has a spontaneous contraction frequency of less than 4 Hz, preferentially less than 2 Hz, even more preferentially less than 1.7 Hz, in particular less than 1 Hz, and notably less than 0.5 Hz and possibly less than 0.25 Hz. This tissue contraction frequency is low, which has a great advantage for its implantation in the heart. Indeed, such a frequency makes it possible to avoid arrhythmia at the moment when the compacted tissue according to the invention is grafted into the heart to be treated.

The average heart rate of a human adult is between 60 and 100 beats per minute (1 to 1.7 Hz). The low contraction frequency of the cardiac compacted tissues according to the invention reduces the risk of arrhythmia during a transplant of the tissues or cells obtained from these tissues. According to one embodiment, with a spontaneous beating frequency of the tissue according to the invention less than the heart rate of the patient (recipient), this risk of arrhythmia is further reduced.

Figure 5:
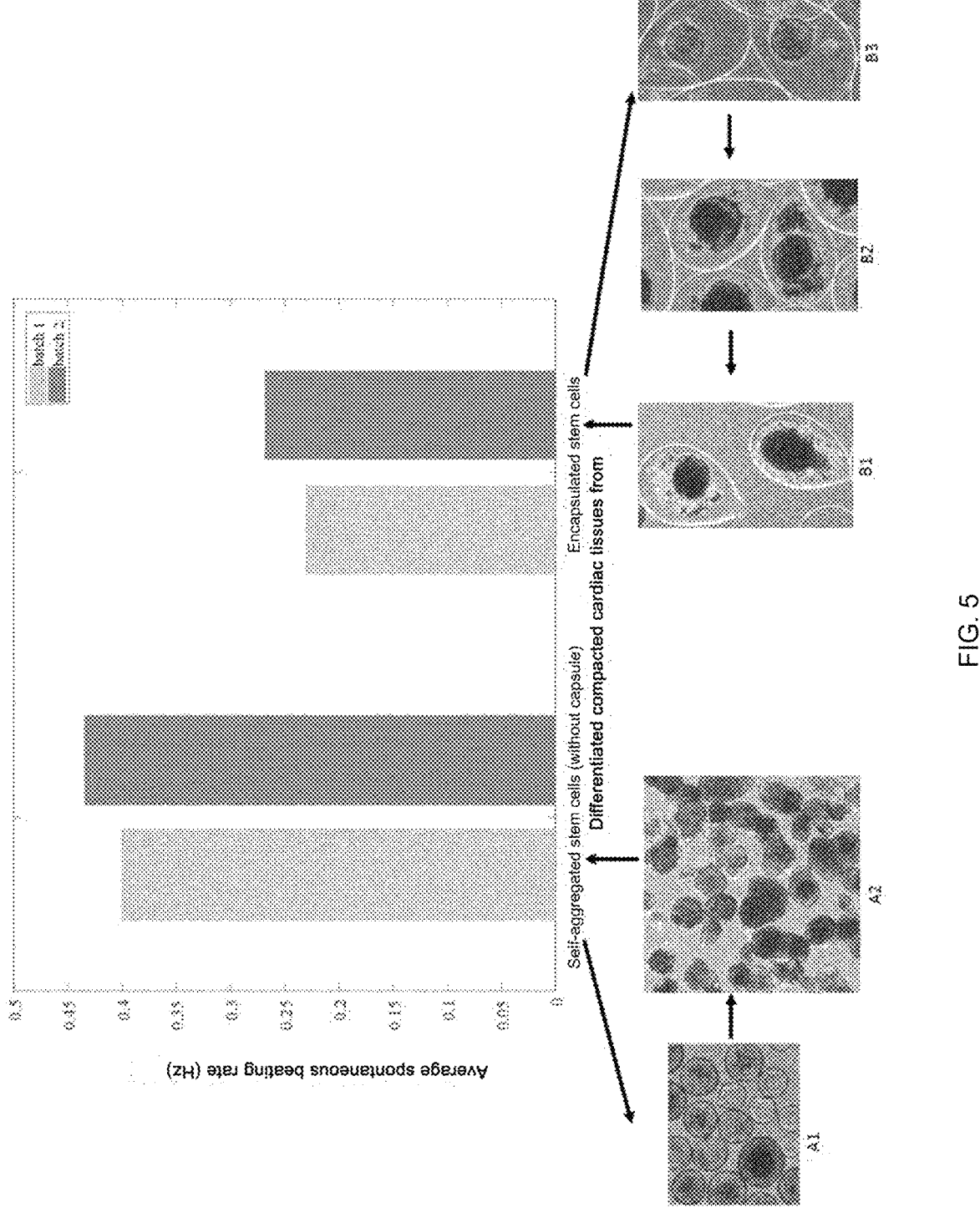
FIG. 5 comprises:
   a graph which represents the beat frequency of tissues and/or cells obtained from a series of phase-contrast microscopy images (at a frequency of at least 30 images per second) on a standard table microscope with 4× magnification, and
   phase-contrast microscopy images taken at 4× magnification showing the encapsulated or free stem cells at the beginning of the differentiation (the outermost), and the compacted tissues according to the invention approximately 2 weeks after the start of differentiation (A1: Aggregates of non-encapsulated stem cells; A2: Compacted cardiac tissue derived from these aggregates; B1: Compacted cardiac tissue in capsules; B2: microcompartments containing cardiac cells undergoing differentiation; B3: encapsulated stem cells).

The reduction in the frequency of spontaneous beats is associated with the maturity of cardiomyocytes derived from human stem cells, as the 3D culture environment improves the maturation of cardiomyocytes. According to the invention, the encapsulation also makes it possible to reduce the contractile frequency of the compacted cardiac tissue. FIG. 5 shows that for a given starting cell population, differentiated cardiomyocytes within a microcompartment/capsule (from encapsulated human pluripotent stem cells) have a spontaneous beating rate slower than the differentiated cardiomyocytes with the same protocol (and the same initial batch of human pluripotent stem cells) but in free suspension culture. Thus, differentiation into cardiomyocytes from encapsulated stem cells reduces spontaneous contractile frequency.

The human pluripotent stem cells secrete signaling molecules during the cardiac differentiation process, which generate a specific paracrine microenvironment necessary for the success of differentiation (Kempf, H. et al. Bulk cell density and Wnt/TGFbeta signalling regulate mesendodermal patterning of human pluripotent stem cells. *Nature Communications* 7, (2016)). The presence of the capsule helps to increase and maintain a local concentration of these paracrine factors, which improves the phenotype of differentiation, resulting in the reduction of the spontaneous beating frequency.

The compacted cardiac tissue according to the invention can remain spontaneously contractile for several months. Thus, the product is stable over time.

According to one variant, cardiac differentiation within the microcompartment may be implemented and/or combined with other techniques, such as electrical stimulation and metabolic or hormonal interventions. The combination with such techniques can make it possible to further reduce the frequency of the spontaneous beats of the compacted cardiac tissue according to the invention before the transplant.

The compacted tissue of cardiac human cells according to the invention can be encapsulated totally or partially in an outer hydrogel layer. The hydrogel capsule may be the original one of the human cellular microcompartment during cardiac differentiation, or it may be a new hydrogel layer if the initial hydrogel layer has been removed, then reencapsulation at any stage of the method.

The encapsulation of the compacted heart cells according to the invention makes it possible to protect the tissue, to maintain the spontaneous contraction frequency of less than 4 Hz, preferentially less than 2 Hz, even more preferentially less than 1 Hz, and in particular less than 0.5 Hz. It may be less than 0.25 Hz. The mechanism according to which the contraction frequency is limited can be linked to the 3D structuring via i) the electrical continuity of the cytoplasmic cells of the cardiac cells, ii) and/or the limitation of the amount of calcium available per cell in the intercellular space of the compacted tissues iii) and/or the mechanical strength related to the mechanical continuity of the cytoskeleton elements of the cardiac cells. The encapsulation of the compacted cardiac tissue according to the invention also makes it possible to control the size of the compacted tissue, which improves retention, integration and cell survival when injected into the heart, in particular in comparison to the single cell injections, which increases the effectiveness of the cardiac cell therapy with the compacted tissues according to the invention.

According to one embodiment, the compacted tissue of cardiac human cells according to the invention is not encapsulated in an outer hydrogel layer. In particular, the capsule is preferentially removed before use in order to allow the compacted tissue cells to be implanted in the heart after a transplant.

The compacted human cardiac cell tissue according to the invention is preferentially totally or partially surrounded by an isotonic aqueous solution layer, such as an extracellular matrix. This isotonic aqueous solution layer is located between the compacted tissue of human cardiac cells and the hydrogel layer when the compacted cardiac tissue is encapsulated.

The compacted cardiac tissue according to the invention is in three dimensions. It preferentially has a spherical or elongated shape. According to a preferred embodiment, the compacted tissue of cardiac human cells has the shape of a spheroid, ovoid, cylinder, or sphere.

An example of a compacted tissue according to the invention is shown in FIG. 4. In this example, the compacted tissue according to the invention is surrounded by an isotonic aqueous solution layer and an outer hydrogel layer.

Preferentially, it has a diameter or a smallest dimension of between 10 μm and 1 mm, preferentially between 100 μm and 700 μm. This smallest dimension is important for its survival, in particular to promote the survival of cardiac cells within cardiac tissue and optimize reorganization as well as vascularization of cardiac tissue after implantation in the heart.

Its largest dimension is preferentially greater than 10 μm, more preferentially between 10 μm and 1 m, even more preferentially between 10 μm and 50 cm. According to one embodiment, the largest dimension is compatible with the size of the member and is therefore less than 30 cm (between 10 μm and 30 cm).

The encapsulation of a controlled number of stem cells and/or their re-encapsulation makes it possible to control the desired size and shape of the cardiac tissues obtained. Thus, the size of the cardiac tissues according to the invention can vary depending on the therapeutic use envisaged.

The compacted human cardiac cell tissue according to the invention can be frozen, to promote storage thereof.

Advantageously, the invention makes it possible to produce a large number of quality human cardiac tissues by protecting the tissue units throughout their production by differentiation of pluripotent cells into cardiac cells.

Figure 7:
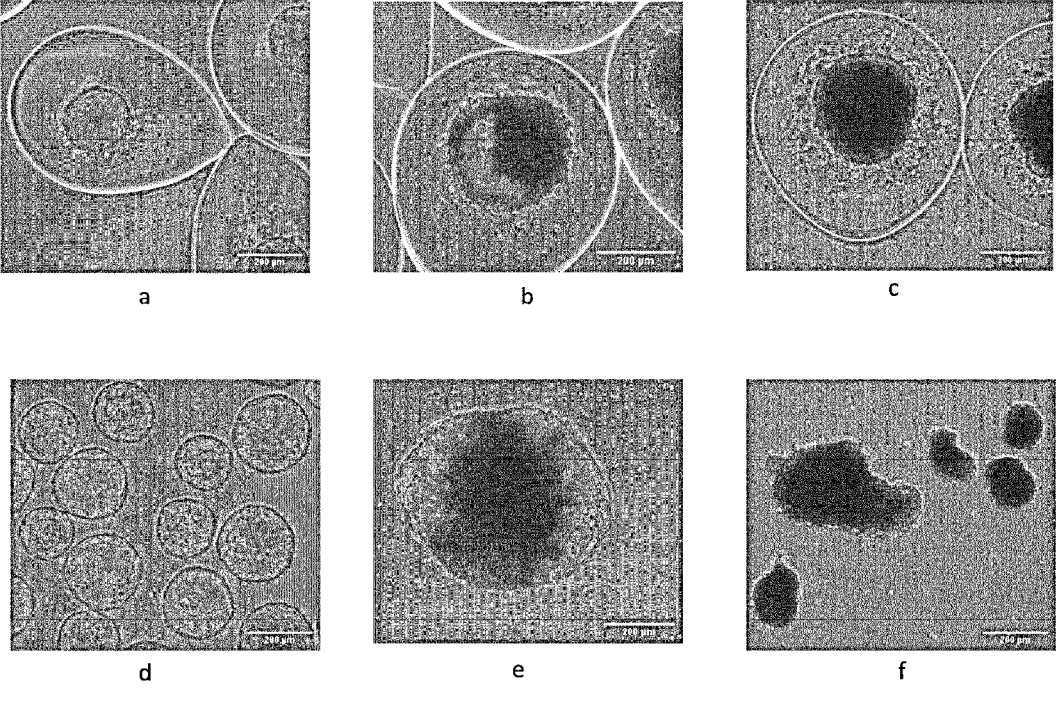
FIG. 7 comprises phase-contrast microscopy images at 4× magnification. The three images of the top row (a, b and c) are images of encapsulated cells. The three images of the bottom row (d, e and f) are images of non-encapsulated cells. The images of the left column (a and d) represent stem cells induced at the start of differentiation into cardiac cells. The images of the middle column (b and e) represent human cells undergoing cardiac differentiation, 3 to 7 days after differentiation was initiated. The images of the right column (c and f) represent differentiated cardiac tissues.
Figures 8, 9:
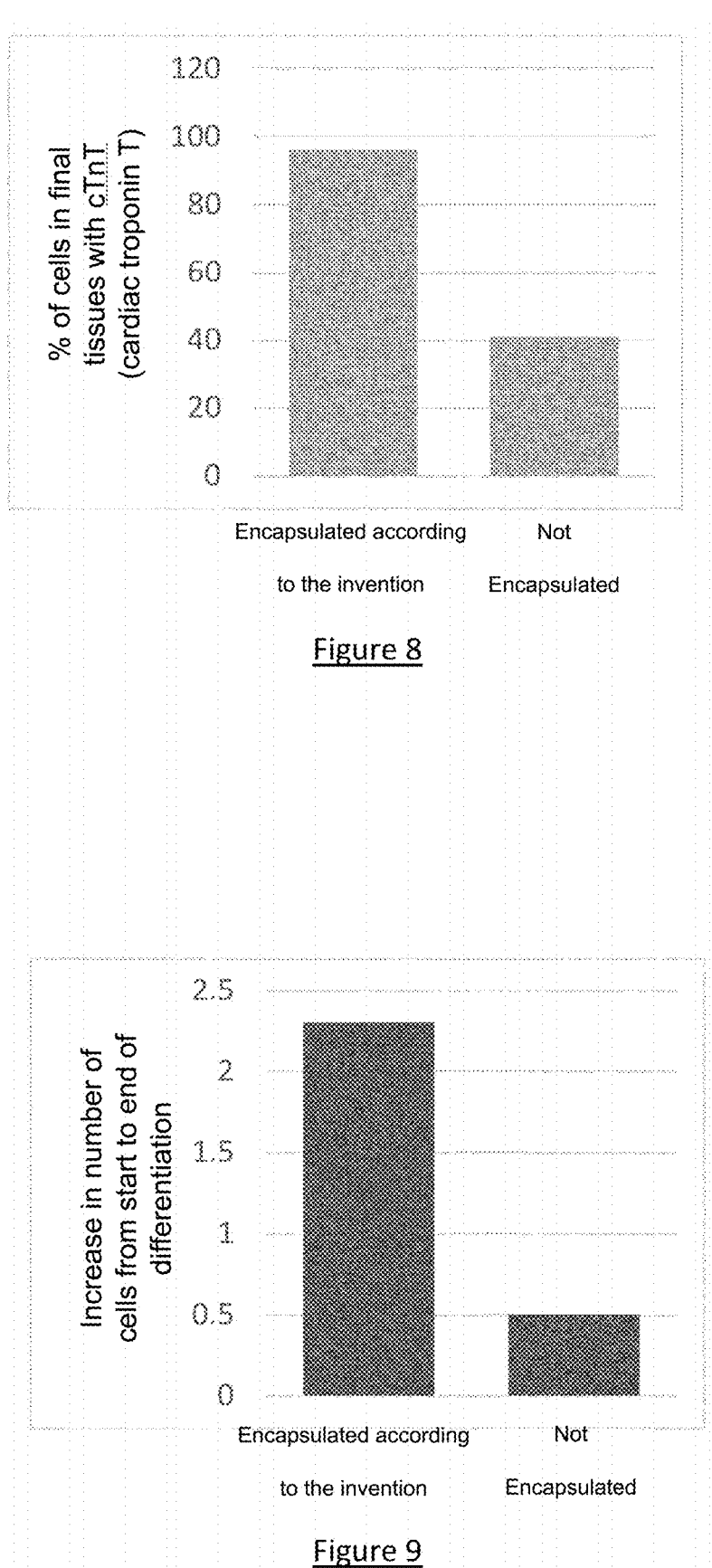
FIG. 8 is a graph which represents the percentage of cells in the tissues (obtained such as in FIGS. 7c and 7f) expressing cardiac troponin C: at left, tissues according to the invention, encapsulated (image 7c); at right, non-encapsulated tissues (image 7f).
FIG. 9 is a graph which represents the cell amplification rate between the start of the differentiation (obtained as in FIGS. 7a and 7d) in the tissues: at left, tissues according to the invention, encapsulated; at right, non-encapsulated tissues.

FIGS. 7, 8 and 9 show that for a given starting cell population, the tissues obtained within a microcompartment/capsule by passing through a phase undergoing differentiation with the presence of at least one lumen, then a secondary compaction, has a level of cells expressing much more troponin C, compared to differentiated tissues with the same protocol (and the same initial batch of human pluripotent stem cells) but in free suspension culture. Thus, differentiation into cardiomyocytes in microcompartments and/or by a method comprising secondary compaction makes it possible to increase the quality of the cardiac tissues and therefore improves the ability to use them in cell therapy.

The compacted heart cell tissue according to the invention can be dissociated into cells. The dissociation can be carried out according to conventional methods known to a person skilled in the art, in particular using an enzymatic solution making it possible to separate the cells. The enzymes used can, for example, be chosen from trypsin, collagenase, accutase, and mixtures thereof. The dissociated cells are preferentially used in suspension or integrated into a gel such as, for example, a collagen gel or into a patch.

Uses of the Compacted Human Cardiac Cell Tissue According to the Invention

The compacted tissue of cardiac human cells according to the invention can be used as such or to produce a suspension of cardiac cells.

Indeed, the compacted heart cell tissue according to the invention is particularly useful for producing a suspension of cells (graft cells) implantable in the heart of a human being, in particular for the treatment of heart disease. The shape, size and composition of the compacted tissue according to the invention promote homogeneous differentiation with improved yield of cardiac cells within the compacted tissue according to the invention, which may be secondarily dissociated prior to implantation in the heart.

The compacted tissue of cardiac human cells according to the invention is also particularly useful for use as such as an implantable graft in the heart of a human being, in particular for the treatment of heart disease. The shape, size and composition of the compacted tissue according to the invention allow the survival of cardiac cells within the compacted tissue according to the invention, before implantation and the success of implantation, reorganization and vascularization of the graft once implanted in the heart.

Another object of the invention is therefore the compacted tissue of human cardiac cells for use, as such or after dissociation in the form of a suspension of cells, in therapy, in particular in cellular therapy, as a drug, in particular its use in the treatment and/or prevention of heart disease, in particular in a patient in need thereof, and preferentially in the treatment and/or prevention of ischemic heart disease.

Figure 6:
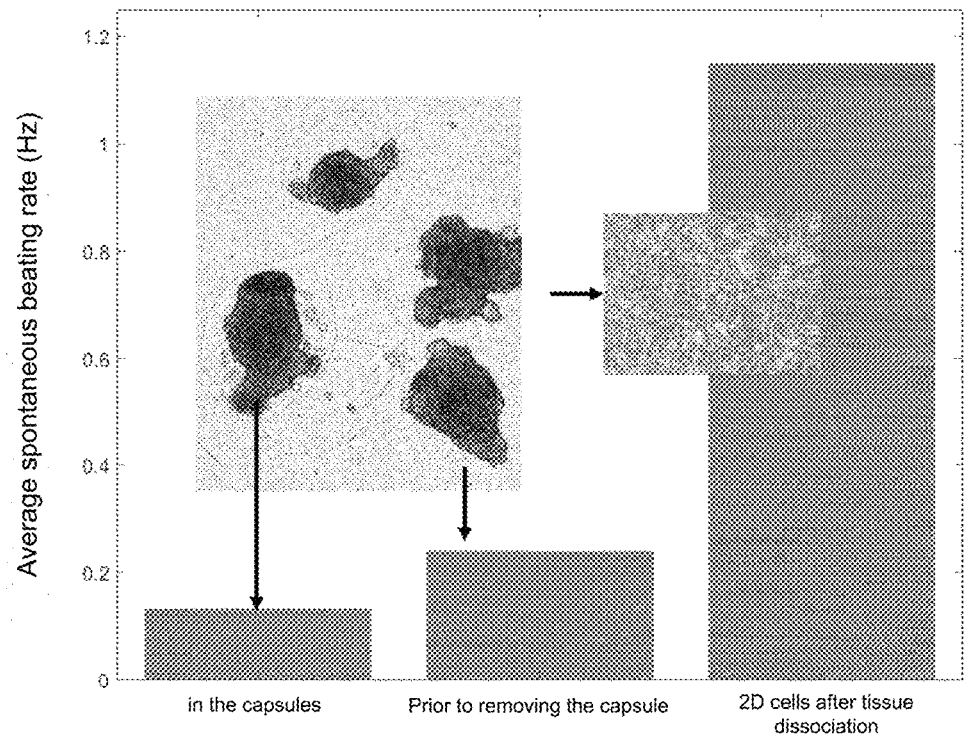
FIG. 6 comprises:
   a graph which represents the beat frequency of tissues and/or cells obtained from a series of phase-contrast microscopy images (at a frequency of at least 30 images per second) on a standard table microscope with 4× magnification, and
   phase-contrast microscopy images taken at 4× magnification. The left image shows the differentiated compacted cardiac tissues in the capsule from encapsulated hiPSCs. The right image shows the cells obtained by dissociating compacted cardiac tissues according to the invention.

Although the dissociated cells obtained from the tissues according to the invention can be used, they have a higher spontaneous contraction frequency than the compacted cardiac tissues. The slow spontaneous beating rate of the differentiated cardiomyocytes within the capsule is not maintained when the cells are dissociated and cultivated in 2D conditions (FIG. 6).

Treatment means a preventive, curative or symptomatic treatment, that is any act intended to improve the outlook of a person temporarily or permanently, and preferentially also to eradicate the disease and/or stop or delay the progression of the disease and/or promote the regression of the disease.

Indeed, the compacted tissues of cardiac human cells according to the invention can be used for the treatment of cardiac diseases in humans, in particular diseases having caused ischemia of at least part of the heart, such as infarction, for example, to replace damaged areas.

The treatment consists in implanting or grafting the compacted tissues according to the invention or the cells obtained by their dissociation into the heart, in the region of the ventricles of the heart, in particular the left ventricle, or of integrating them into a patch positioned on said ventricles, ideally between the visceral pericardium and the muscle tissue of the ventricle, or what remains of it in a pathological situation. A surgical implantation device suitable for implantation in the heart is very preferentially used. These may in particular be needles, cannulae, or other devices making it possible to deposit the compacted tissues according to the invention or the cells obtained by dissociating the compacted tissues according to the invention, into the heart, for example those used for the implantation of stents in surgical arteries or microimplants.

According to one example embodiment, the implantation can be carried out by direct myocardial injection, in particular by sternotomy or with a catheter-based device: the cardiac compacted tissues according to the invention or the cells obtained from these tissues (with or without the addition of other types of cells) are injected into the median wall of the left ventricle of the patient at one or more locations.

According to another example embodiment, the implantation may be performed using an epicardial patch. The compacted cardiac tissues according to the invention or the cells obtained from these tissues (with or without the addition of other types of cells) are used in the formation of patches. These patches can then be placed on the epicardial surface of the patient's left ventricle, either by sternotomy or by a surgical procedure involving an incision and an injection of the patch into the thoracic cavity.

In one embodiment, during a single implantation, between 1 and 1,000,000 compacted tissue units according to the invention are implanted.

In one embodiment, during a single implantation, between $10^4$ and $10^{10}$ cells obtained by dissociation of compacted tissue units according to the invention are implanted.

If necessary, it is possible to carry out several simultaneous or successive implantations in different zones of the heart, in particular in the case where several separate zones are touched or if the zone on which the transplant must be carried out is too extensive to carry out a transplant only at a location.

Likewise, on the same zone, if a single transplant is not sufficient, several implantations can be carried out again on the same zone, in a more or less significant period of time.

The implantation of compacted cardiac tissues according to the invention allows patients suffering from cardiac diseases, and in particular ischemic heart diseases, to clinically improve the cardiac function, in particular:

increasing the contractile performance of the heart cells (which may be measured for example by the ejection fraction of the left ventricle) and/or increasing the thickness of the ventricular wall.

Thus, advantageously, the invention makes it possible to improve the overall health and life of the patient, while limiting the risk of arrhythmia induced by the transplant.

According to another aspect, the compacted tissues according to the invention can be useful as a cardiac tissue model in particular:

to test drugs and drug candidates for efficacy on heart disease and/or effect on the heart, and/or to test the cardiac toxicity of substances, compounds, compositions or drugs.

Thus, the invention also relates to these uses.

The invention is now illustrated by examples.

EXAMPLES

Several examples of microcompartments according to the invention are presented in FIGS. 1 to 3, and examples of compacted tissues are presented in FIG. 4.

Example 1

Figure 1B:
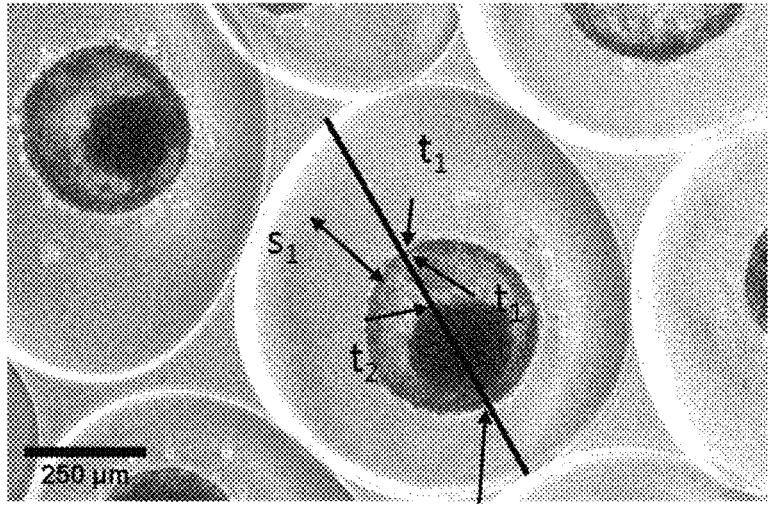

The image of FIG. 1*b* a phase-contrast microscopy image of a microcompartment according to the invention taken at 4× magnification. It was taken 5 days after the start of the differentiation (8 days after the initial encapsulation of the stem cells). The steps used to obtain the microcompartment shown in this figure are as follows:

1. The human-induced pluripotent stem cells were encapsulated in an alginate hydrogel (without adding extracellular matrix at the time of encapsulation).
2. The encapsulated stem cells were cultivated in culture media of stem cells (mTeSR1) for 3 days.
3. On the 3rd day, the culture medium was changed from stem cell media to a cardiac differentiation medium containing a WNT-activating molecule (CHIR99021). The medium is an RPMI medium with B27 supplement without insulin with CHIR99021 This is considered to be day 0 of differentiation.
4. On the 2nd day of differentiation, the medium was changed to a cardiac differentiation medium without a WNT-activating molecule. The medium is an insulin-free RPMI medium with B27 supplement
5. On the 3rd day of differentiation, the medium was changed to a cardiac differentiation medium containing a molecule that inhibits the WNT pathway (WNT-059 or IWR1). The medium is an insulin-free RPMI medium B27 with WNT-059 or IWR1.
6. On the 5th day of differentiation, the photo of FIG. 1*b* was taken by phase-contrast microscopy of a microcompartment according to the invention at 4× magnification.

Example 2

Figure 2B:
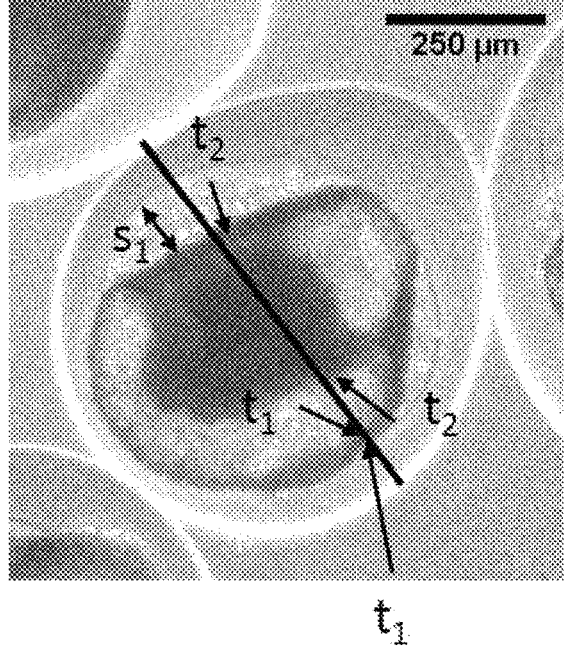
Figure 2C:
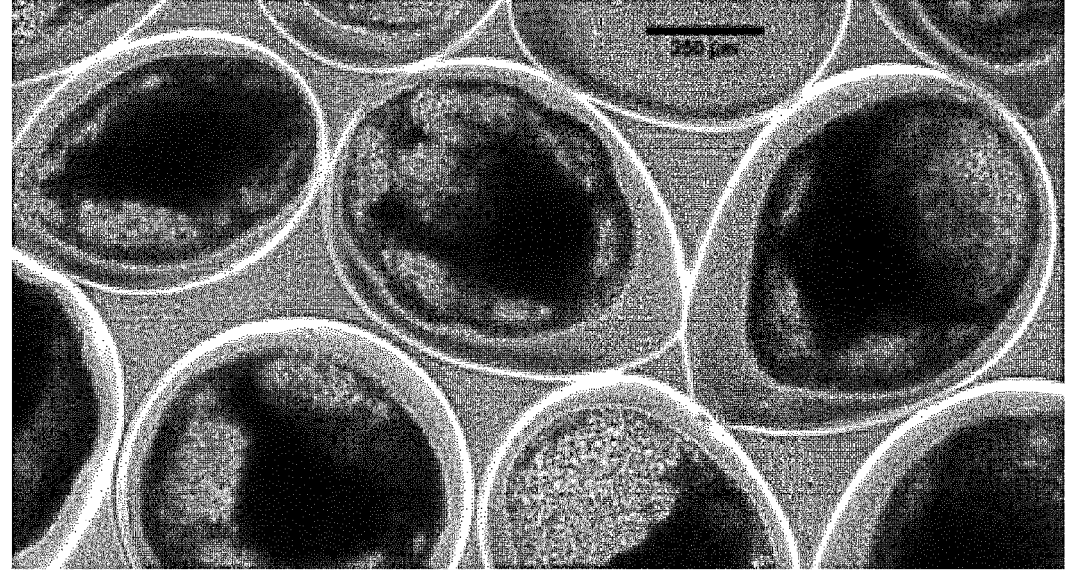
FIG. 2c is a phase-contrast microscopy image of a plurality of microcompartments according to the invention, taken at 4× magnification, each microcompartment with different morphologies.

The images of FIGS. 2*b* and 2*c* are phase-contrast microscopy images of a microcompartment according to the invention taken at 4× magnification. They were taken 5 days after the start of differentiation (11 days after the initial encapsulation of the stem cells). The steps used to obtain the microcompartment shown in these figures are as follows:

1. The human-induced pluripotent stem cells were encapsulated in an alginate hydrogel (adding extracellular matrix at the time of encapsulation).
2. The encapsulated stem cells were cultivated in culture media of stem cells (mTeSR1) for 6 days.
3. On the 6th day, the culture medium was changed from stem cell media to a cardiac differentiation medium containing a WNT-activating molecule (CHIR99021).

The medium is an RPMI medium with B27 supplement without insulin with CHIR99021 This is considered to be day 0 of differentiation.
4. On the 2nd day of differentiation, the medium was changed to a cardiac differentiation medium without a WNT-activating molecule. The medium is an insulin-free RPMI medium with B27 supplement
5. On the 3rd day of differentiation, the medium was changed to a cardiac differentiation medium containing a molecule that inhibits the WNT pathway (WNT-059 or IWR1). The medium is an insulin-free RPMI medium B27 with WNT-059 or IWR1.
6. On the 5th day of differentiation, the photos of FIGS. 2*b* and 2*c* were taken by phase-contrast microscopy of a microcompartment according to the invention at 4× magnification.

Example 3

Figure 3B:
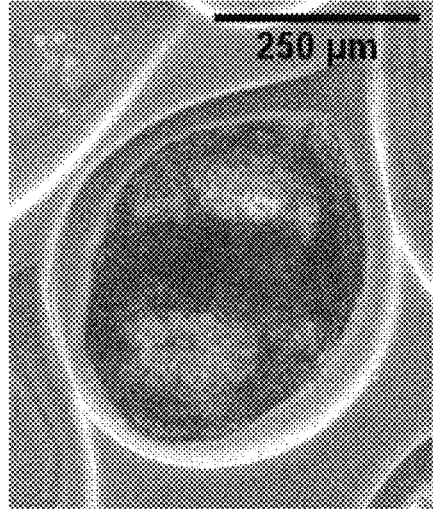

The image of FIG. 3*b* is a phase-contrast microscopy image of a microcompartment according to the invention taken at 4× magnification. It was taken 5 days after the start of differentiation (11 days after the initial encapsulation of the stem cells). The steps used to obtain the microcompartment shown in these figures are the same as cells in order to obtain FIGS. 2*b* and 2*c*. The difference lies in a larger number of encapsulated stem cells.

Example 4

Figure 4A:
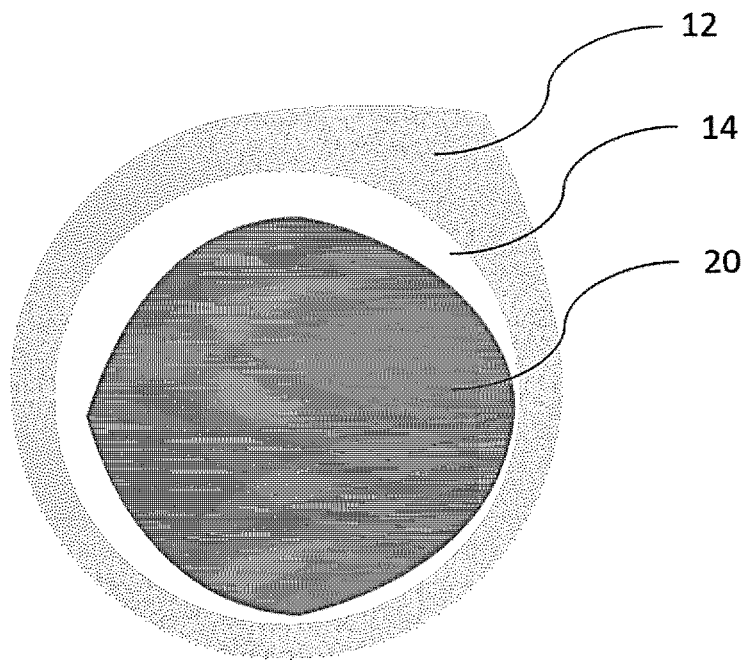
FIG. 4a is a schematic representation of a sectional view of a compacted tissue according to the invention, corresponding to the photo shown in FIG. 4b, with an outer hydrogel layer 12, an isotonic aqueous solution layer 14, a compacted tissue of differentiated cardiac cells 20.
Figure 4B:
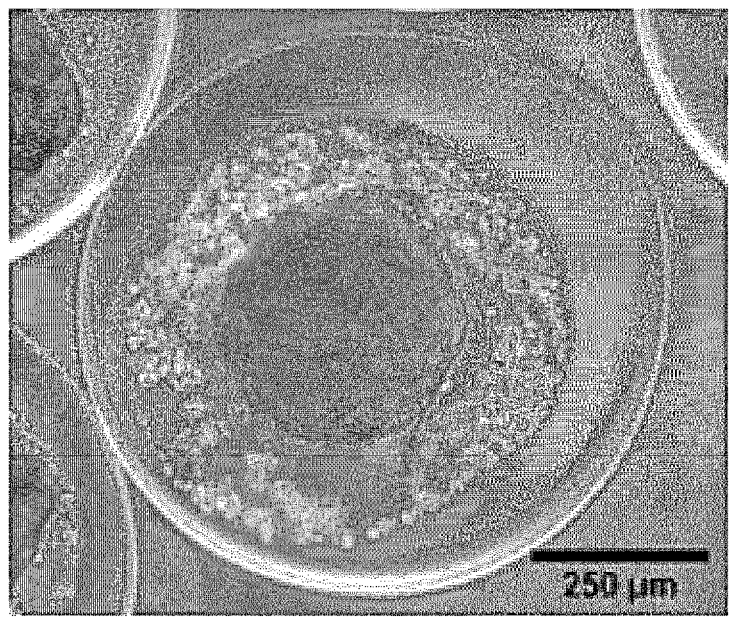
Figure 4C:
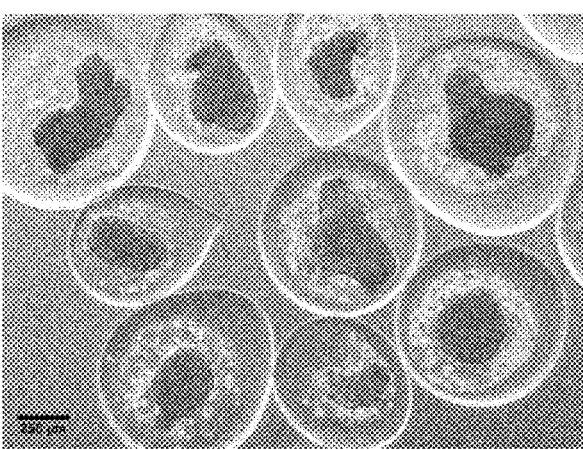
FIG. 4c shows phase-contrast microscopy images taken at 4× magnification of compacted tissues according to the invention in microcompartments.
Figure 4C:
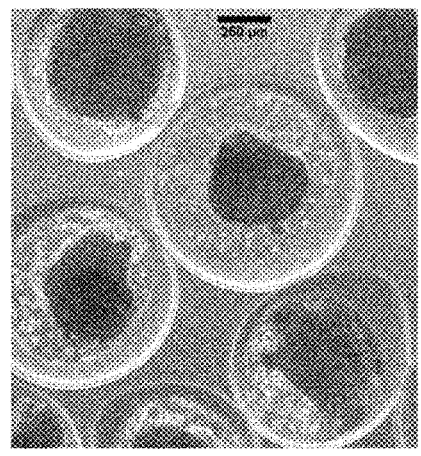
Figure 4C:
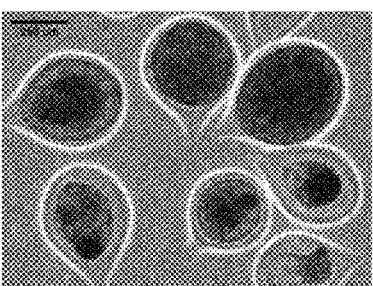

FIGS. 4*b* and 4*c* are phase-contrast microscopy images taken at 4× magnification of compacted tissues according to the invention in microcompartments. The compacted tissues were obtained by continuing the differentiation beyond day 5 (already described in FIGS. 1, 2 and 3):

1. On the 7th day of differentiation, the culture medium was replaced with an RPMI medium with B27 supplement with insulin
2. The medium was changed every 2-3 days until imaging.

The images presented in FIG. 4 relate to compacted tissues 14 days after the start of differentiation.

Comparative Tests: Spontaneous Beating Rate

FIG. 5 shows that for a given starting cell population, differentiated cardiomyocytes within the capsule (from encapsulated hiPSC) have a spontaneous beating rate slower than differentiated cardiomyocytes with the same protocol (and from the same initial batch of hiPSC) but in free culture suspension. The beating rate (in Hz) was obtained from a series of phase-contrast microscopy images (at a frequency of at least 30 images per second) on a standard table microscope with 4× magnification, and The images are phase-contrast microscopy images taken at 4× magnification showing the encapsulated or free stem cells at the beginning of the differentiation (the outermost), and the final compacted tissues approximately 2 weeks after the start of differentiation (the innermost ones). In the case of the encapsulated differentiation process, an intermediate step with a microcompartment according to the invention is presented at the differentiation day 5.

FIG. 6 shows that the slow speed of spontaneous beating of differentiated cardiomyocytes in the capsule is slightly increased after removing the capsule, and greatly increased after the cells have been dissociated and placed in 2D culture. Thus, the compacted cardiac tissues have a slower beating rate than that of the isolated cells obtained by dissociation of said tissues. The beating rate (in Hz) was obtained from a series of phase-contrast microscopy images (at a frequency of at least 30 images per second) on a standard table microscope with 4× magnification, and The beating rate for the encapsulated and then unencapsulated compacted cardiac tissues according to the invention was taken approximately 3 weeks after the start of differentiation. About 3 weeks after the differentiation, a sub-population of compacted tissues according to the invention was dissociated and placed under 2D culture conditions for 1 week before recording the beating rate. The images are phase-contrast microscopy images taken at 4× magnification. The left image shows the differentiated compacted cardiac tissues in the capsule from encapsulated hiPSCs. The right image shows the cells obtained from a subset of the initial encapsulated reconstructed cardiac tissues after having been placed under 2D culture conditions.

Comparative Tests: Topology, Cell Amplification and Number of Cells Expressing Troponin C Comparative tests with the same differentiation method under the same experimental conditions were carried out to compare the differentiation into cardiac cells and the tissues obtained in three dimensions with or without encapsulation.

All the cultures were produced from the same initial cells taken in a 2D culture. Aggregates obtained in 3D are cultured (without adding any matrix) with or without capsules in a stirred suspension culture (stirring at 55 rpm). The same cell density is used at the start (e6 cells/mL of medium) on day 0 of the differentiation (images a) and e)). The same differentiation protocol is applied in both conditions (with and without capsule).

FIG. 7 shows phase-contrast microscopy images at 4× magnification. The three images of the top row (a, b and c) are images of encapsulated cells according to the invention.

The three images of the bottom row (d, e and f) are images of non-encapsulated cells.

The images of the left column (a and d) represent stem cells induced at the start of differentiation into cardiac cells.

The images of the middle column (b and e) represent human cells undergoing cardiac differentiation, 3 to 7 days after differentiation was initiated.

The images of the right column (c and f) represent differentiated cardiac tissues.

It is noted that the topology is different with and without encapsulation according to the invention. Without encapsulation, there is no lumen during differentiation, and the cardiac tissue obtained at the end of differentiation has a very different shape.

In FIG. 8, it can be seen that the percentage of cells in the tissues (obtained such as in FIGS. 7c and 7f) expressing cardiac troponin C is greater than 90% under the conditions of the invention while it is 40% for the cardiac tissues obtained under the same conditions but without encapsulation.

In FIG. 9, it is found that the cell amplification rate between the start of the differentiation is greater than 2 under the conditions of the invention while it is less than 0.5 for the cardiac tissues obtained under the same conditions but without encapsulation.

The invention claimed is:

1. A three-dimensional cellular microcompartment (10) successively comprising, organized around at least one lumen (18):
 at least one inner layer (16) of human cells undergoing cardiac differentiation, expressing at least one gene chosen from PDGFRα, MESP-1, NKX2-5, GATA4, MEF2C, TBX20, ISL1, and TBX5,
 at least one intermediate layer (14) of isotonic aqueous solution, and
 at least one outer hydrogel layer (12),
 the inner layer having a variable thickness and the ratio between the largest thickness (t2) and the smallest thickness (t1) of the inner layer being greater than or equal to 2, the smallest thickness (t1) and the largest thickness (t2) of the inner layer being the smallest and the largest of the inner layer thicknesses measured along a segment (22) passing through the geometric center of the cellular object formed by the inner layer and the one or more lumen(s) (18, 18-1, 18-2), between the interface of the inner layer and of the intermediate layer and the interface of the inner layer and of a lumen (18, 18-1, 18-2), and/or between the interface of the inner layer and of a lumen (18-1) and the interface of the inner layer and of another lumen (18-2).

2. The cellular microcompartment (10) according to claim 1, characterized in that the ratio between the largest thickness (t2) and the smallest thickness (t1) of the inner layer (16) is greater than or equal to 5.

3. The cellular microcompartment (10) according to claim 1, characterized in that the intermediate layer (14) of isotonic aqueous solution contains peptide or peptidomimetic sequences capable of binding to integrins.

4. The cellular microcompartment (10) according to claim 1, characterized in that it comprises at least two lumens (18-1, 18-2).

5. The cellular microcompartment (10) according to claim 1, characterized in that the human cells of the inner layer (16) were obtained from human pluripotent stem cells.

6. The cellular microcompartment (10) according to claim 1, characterized in that it is closed.

7. The cellular microcompartment (10) according to claim 1, characterized in that the outer layer (12) made of hydrogel comprises at least alginate.

8. The cellular microcompartment (10) according to claim 1, characterized in that it has a spherical or elongated shape.

9. The cellular microcompartment (10) according to claim 8, characterized in that it is a hollow spheroid, a hollow ovoid, a hollow cylinder or a hollow sphere.

10. The cellular microcompartment (10) according to claim 1, characterized in that it has a diameter or a smallest dimension of between 10 μm and 1 mm.

11. The cellular microcompartment (10) according to claim 1, characterized in that it has a largest dimension of between 10 μm and 50 cm.

12. The cellular microcompartment (10) according to claim 1, characterized in that the number of human cells undergoing cardiac differentiation in the inner layer (16) is between 1 and 100,000 cells.

13. The cellular microcompartment (10) according to claim 1, characterized in that the number of human cells undergoing cardiac differentiation in the inner layer is between 50 and 50,000 cells.

14. A series of cellular microcompartments (10) comprising at least two cellular microcompartments according to claim 1.

15. The series of cellular microcompartments (10) according to claim 14, characterized in that the microcompartments are in a convective culture medium.

16. The series of cellular microcompartments (10) according to claim 14, characterized in that the microcompartments are in the culture medium in a closed chamber.

* * * * *